US008417536B2

(12) United States Patent
Seward et al.

(10) Patent No.: US 8,417,536 B2
(45) Date of Patent: Apr. 9, 2013

(54) ULTRASOUND LABORATORY INFORMATION MANAGEMENT SYSTEM AND METHOD

(75) Inventors: James B. Seward, Rochester, MN (US); Bijoy K. Khandheria, Rochester, MN (US); James A. Koerner, Rochester, MN (US); Trudy J. Wellik, Rochester, MN (US); William H. Hansen, Rochester, MN (US); Gregory Gilman, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 1662 days.

(21) Appl. No.: 10/150,646

(22) Filed: May 17, 2002

(65) Prior Publication Data

US 2002/0198454 A1 Dec. 26, 2002

Related U.S. Application Data

(60) Provisional application No. 60/292,177, filed on May 18, 2001.

(51) Int. Cl.
*G06Q 50/00* (2012.01)
(52) U.S. Cl.
USPC .................................. 705/2; 705/3; 600/300
(58) Field of Classification Search .................. 705/2, 3
See application file for complete search history.

(56) References Cited

U.S. PATENT DOCUMENTS

| 5,322,066 | A | | 6/1994 | Miyataka et al. |
| 5,469,353 | A | | 11/1995 | Pinsky et al. |
| 5,483,443 | A | * | 1/1996 | Milstein et al. ................... 705/3 |
| 5,492,125 | A | | 2/1996 | Kim et al. |
| 5,522,392 | A | | 6/1996 | Suorsa et al. |
| 5,528,302 | A | | 6/1996 | Basoglu et al. |
| 5,628,322 | A | | 5/1997 | Mine |
| 5,669,384 | A | | 9/1997 | Park et al. |
| RE35,720 | E | | 2/1998 | Arenson et al. |
| 5,715,823 | A | * | 2/1998 | Wood et al. ................... 600/437 |
| 5,720,291 | A | | 2/1998 | Schwartz |
| 5,776,063 | A | | 7/1998 | Dittrich et al. |
| 5,810,008 | A | | 9/1998 | Dekel et al. |
| 5,851,186 | A | | 12/1998 | Wood et al. |

(Continued)

FOREIGN PATENT DOCUMENTS

EP 0 844 581 5/1998

*Primary Examiner* — David Rines
(74) *Attorney, Agent, or Firm* — Quarles & Brady, LLP

(57) ABSTRACT

A multifunctional information management system that integrates a plurality of modules, each of the modules being interfaced via a relational database. The integrated system manages a large volume of business, data, and image information and is capable of being accessed/organized via the Internet. One embodiment of the multifunctional information management system is an ultrasound laboratory information management system (ULIMS) for a medical ultrasound imaging and hemodynamic laboratory, e.g., an echocardiographic or comparable medical laboratory environment, incorporating a multifunctional management system. The ULIMS includes: 1) Scheduling and Workflow Modules; 2) Patient Information and Demographics Modules; 3) Billing Modules; 4) Procedure Information and Referral Diagnosis Modules; and 5) Measurement, Templates and Calculations Modules; 6) Final Impressions and Interpretation Modules; 7) Procedure Report Modules; 8) Serial Studies Module; 9) Research Protocols Module; 10) User Interface and Services Modules; 11) Web Based Modules; 12) Unique Reports Modules; 13) Database Modules; 14) Systems Administration Modules; 15) Security, Privacy and User Configuration Modules; 16) Image Modules; 17) Systems and Technical Support Modules; and 18) Knowledge Base Modules.

5 Claims, 29 Drawing Sheets

U.S. PATENT DOCUMENTS

| | | | | |
|---|---|---|---|---|
| 5,855,557 | A | 1/1999 | Lazenby | |
| 5,860,924 | A | 1/1999 | Quistgaard | |
| 5,861,018 | A | 1/1999 | Feierbach | |
| 5,897,498 | A | 4/1999 | Canfield, II et al. | |
| 5,897,502 | A | 4/1999 | Wong et al. | |
| 5,949,491 | A | 9/1999 | Callahan et al. | |
| 5,967,987 | A | 10/1999 | Sumanaweera et al. | |
| 5,971,923 | A | 10/1999 | Finger | |
| 5,974,389 | A | 10/1999 | Clark et al. | |
| 5,997,480 | A | 12/1999 | Sumanaweera et al. | |
| 6,018,713 | A * | 1/2000 | Coli et al. | 705/2 |
| 6,030,345 | A | 2/2000 | Wang | |
| 6,032,120 | A | 2/2000 | Rock et al. | |
| 6,047,259 | A | 4/2000 | Campbell et al. | |
| 6,171,244 | B1 | 1/2001 | Finger et al. | |
| 6,196,970 | B1 * | 3/2001 | Brown | 600/300 |
| 6,196,972 | B1 | 3/2001 | Moehring | |
| 6,208,974 | B1 | 3/2001 | Campbell et al. | |
| 6,820,235 | B1 * | 11/2004 | Bleicher et al. | 715/501.1 |
| 6,988,088 | B1 * | 1/2006 | Miikkulainen et al. | 706/14 |
| 7,054,823 | B1 * | 5/2006 | Briegs et al. | 705/2 |
| 7,412,396 | B1 * | 8/2008 | Haq | 705/2 |
| 2001/0051881 | A1 * | 12/2001 | Filler | 705/3 |
| 2002/0077849 | A1 * | 6/2002 | Baruch et al. | 705/2 |
| 2003/0055679 | A1 * | 3/2003 | Soll et al. | 705/2 |
| 2003/0208378 | A1 * | 11/2003 | Thangaraj et al. | 705/2 |
| 2004/0260666 | A1 * | 12/2004 | Pestotnik et al. | 706/46 |

* cited by examiner

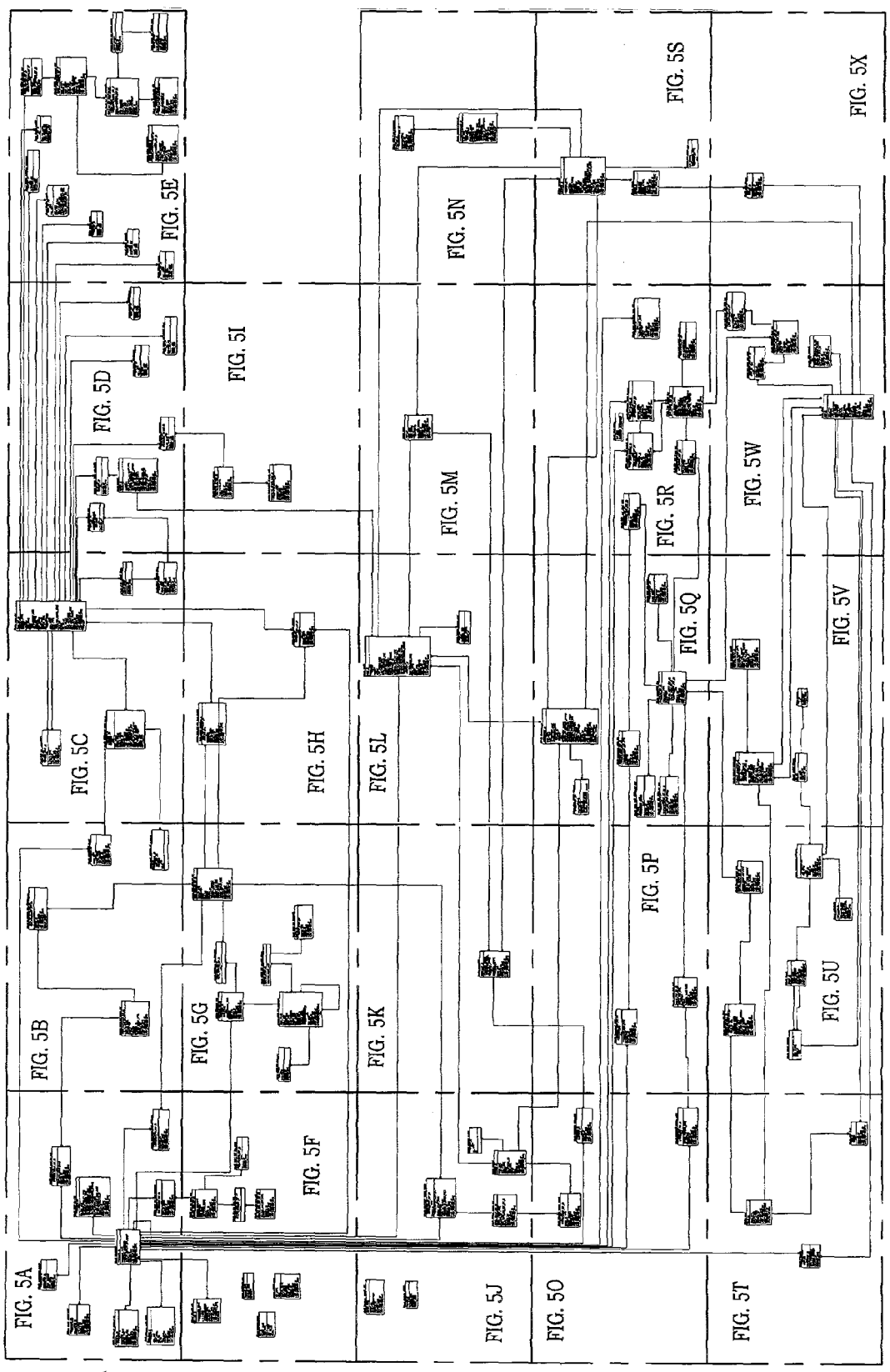

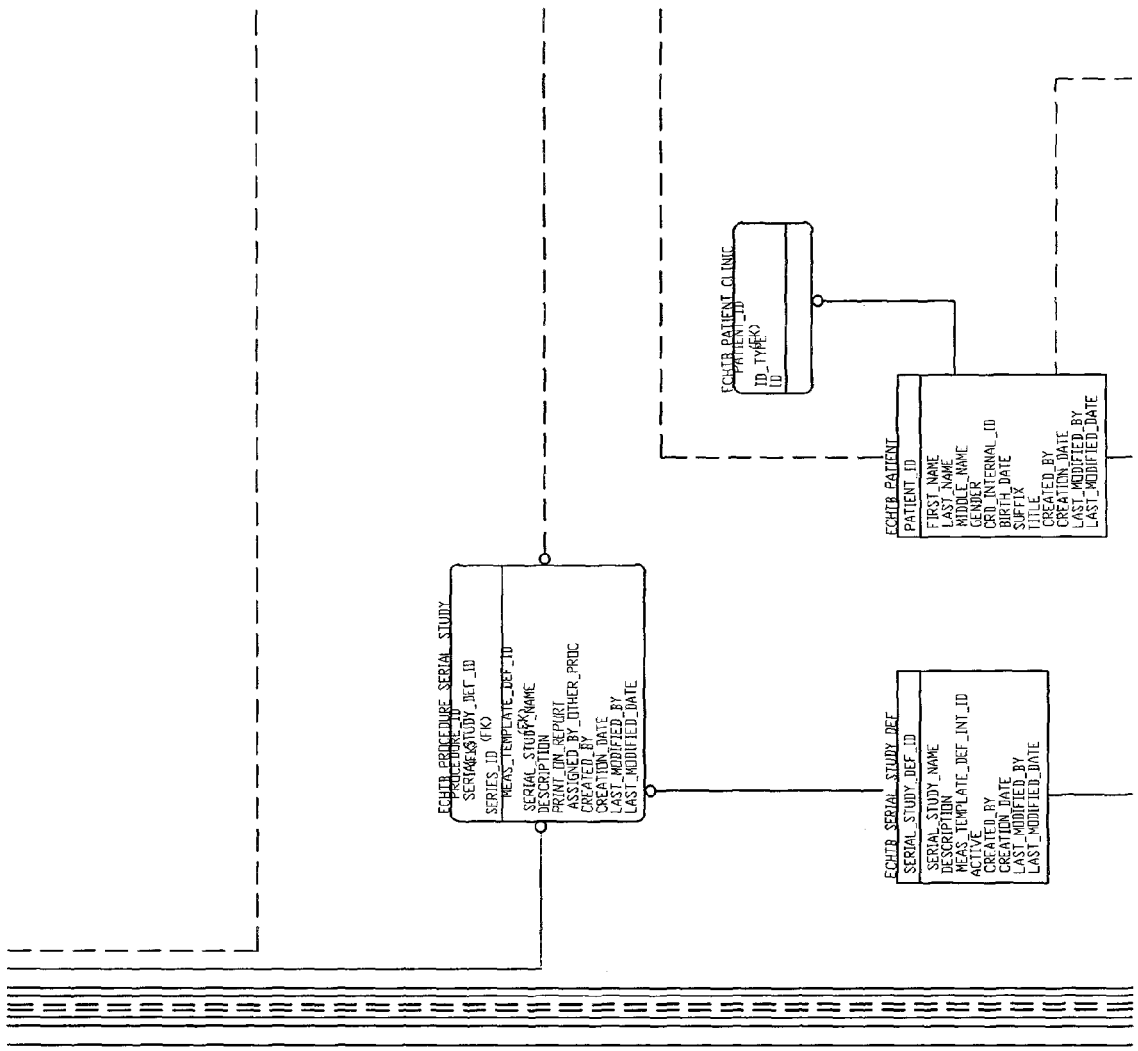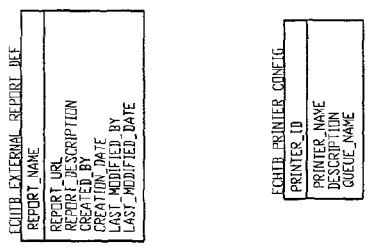
FIG. 5J

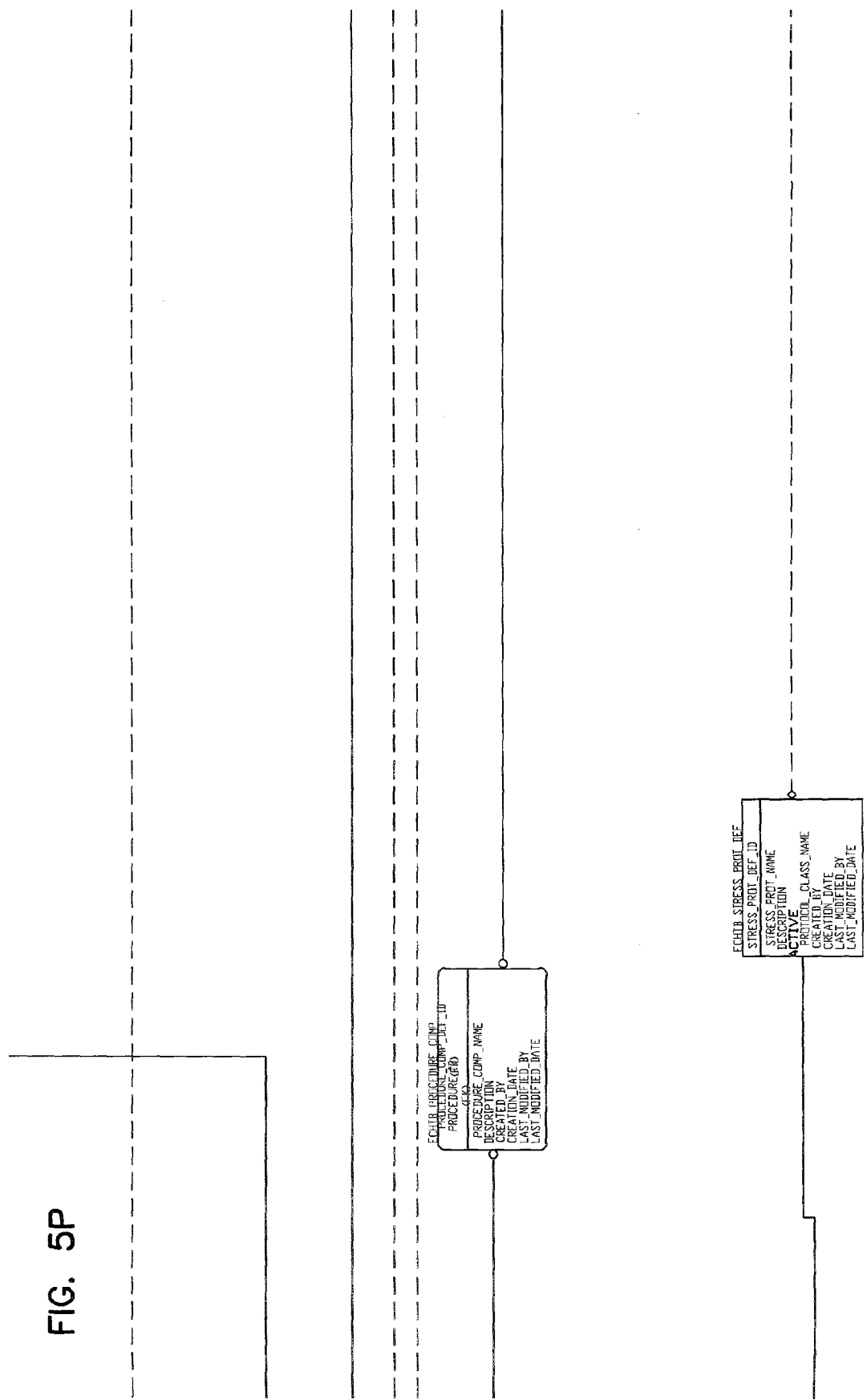

ULTRASOUND LABORATORY INFORMATION MANAGEMENT SYSTEM AND METHOD

FIELD OF THE INVENTION

The present invention relates in general to an information management system and method, and more particularly, to an ultrasound laboratory information management system and method.

BACKGROUND OF THE INVENTION

Medical ultrasound is currently used throughout the practice of modern medicine and one of the most commonly performed examinations. Medical ultrasound is a very safe energy source with no known toxic effects under normal use circumstances. A medical ultrasound laboratory supports a diverse number of functions formally performed by more invasive technologies, e.g., imaging, functional cardiovascular assessment, Doppler hemodynamics, and visualization of blood flow, etc. Ultrasound can be formulated into numerous sizes and shapes in order to accommodate specific applications, e.g., transesophageal echo, intravascular echo, handheld, transvaginal echo, etc. Meanwhile, new innovations, which include multidimensional imaging, miniaturized devices, digital imaging, intravascular and other invasive devices, and the use of tracer contrast agents, have been developed. Therapeutic ultrasound and parametric imaging are also being developed. Today, a large amount of relevant clinical, research and education information can be acquired, collated, stored and transmitted. These diverse applications and functionality, in conjunction with the evolution of computer technology, create a need to increase the efficiency of information management within the field of medical ultrasound.

In order to support numerous functions of a modern ultrasound laboratory, a robust, state-of-the-art information management system is needed. Attempts to develop management systems for medical ultrasound facilities have thus far been fraught with disappointing results. Most current systems are immature and do not bring to bear the full resources of a large clinical laboratory system, such as the Noninvasive Ultrasound Imaging and Hemodynamic Laboratory developed by Mayo Clinic in Rochester, Minn.

There currently is need for an information management system capable of handling diverse ultrasound resources and processes, to collate and database these into a sophisticated and unified application.

It is with respect to these or other considerations that the present invention has been developed.

SUMMARY OF THE INVENTION

In accordance with this invention, the above and other problems were solved by providing a multifunctional information management system that integrates a plurality of modules, each of the modules being interfaced via a relational database. The integrated system manages a large volume of functional, anatomic and work related data, as well as image information. The system is capable of being accessed and organized via an Internet interface.

In one embodiment, the present invention provides an integrated ultrasound laboratory information management system suitable for a medical cardiovascular ultrasound imaging and hemodynamic laboratory, or an echocardiographic or comparable medical ultrasound laboratory environment. The system is capable of supporting patient management, data collection, and final report preparation. The system has the flexibility to support scaleable input of data from multiple sources in multiple locations via wired and wireless connections. The system is also dynamic and can easily be enhanced to grow with a laboratory's capacity and configuration. A final report of the system supports graphics that are accessed via an Internet web browser operating system.

An information management system in accordance with the principles of the present invention is designed and built to fulfill the needs of diverse type of ultrasound laboratory. The system can be distributed to a diverse number of users with varied needs. The system is capable of fulfilling the needs of stand-alone facilities as well as outreach services. Further, the system is scaleable to accommodate projected increase in volume, capacity, personnel, and space. Furthermore, the system is built in components, which can be removed, modified, and/or replaced as desired. Moreover, the system is extensible and does accommodate data, graphic, and image management technology.

Still in one embodiment, a medical ultrasound laboratory information management system is integrated mainly from three parts: a business management part, an ultrasound data management part, and an ultrasound image management part. The business management part of the system manages all aspects from running a small clinic to a very large medical enterprise. Within a medical ultrasound environment, the business management part generally refers to documenting exam encounters, patient demographics, accounting, scheduling, billing, productivity measures, clinical accountability, etc. Immediately connected to these functions are the systems related to accounting, such as a third party billing, coding, documentation, reimbursement, etc. Other related connections include remote access to extended practices and locations, national and international access and communications, etc.

Further in one embodiment, the ultrasound data management part of the system includes acquisition, collation, and reporting of acquired alphanumeric information, such as measurements, hemodynamics, function, flow calculations, derived information, impressions, text descriptors, etc. This is a complex and ever changing aspect of clinical ultrasound examinations. The presentation of data can be tabular, textual, graphic, or pictorial. Further, the presentation of data may continue to evolve such that an information management system of the present invention is designed to accommodate and support a dynamic process. The data is typically used for clinical decision-making. Also, the system of the present invention allows the data to be used for fields such as education, research, treatment, and therapeutics, etc. Accordingly, the data or information in the information management system of the present invention are collated as well as retrieved in a systematic manner.

Further incorporated into the ultrasound data management part of the system is a knowledge based artificial intelligence.

The ultrasound image management part of the system accommodates large-sized documents, such as graphics, still and cinematic pictures, digital documents, parametric information, etc. A large-sized digital document, for example, an image or graphic document that is displayed with a high frame rate (e.g., 200 to 300 images frames per second), is managed by the system of the present invention. All image information are collated as well as retrieved in a systematic manner and treated similar to the other data. The data volume in the image management component is significantly greater than the data volume in the previous two functions.

Yet in one embodiment, all information provided by the business management part, the ultrasound data management part, and the ultrasound image management part are integrated into a single information management system.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there are illustrated and described specific examples of an apparatus in accordance with the invention.

BRIEF DESCRIPTION OF THE DRAWINGS

Referring now to the drawings in which like reference numbers represent corresponding parts throughout:

FIG. 5 illustrates the overall table with a drawing location reference grid comprising 24 tiles. Each tile is labeled 5A through 5X and corresponds to the similarly numbered FIGS. 5A through 5X.

DETAILED DESCRIPTION OF THE PREFERRED EMBODIMENT

Figure 1:
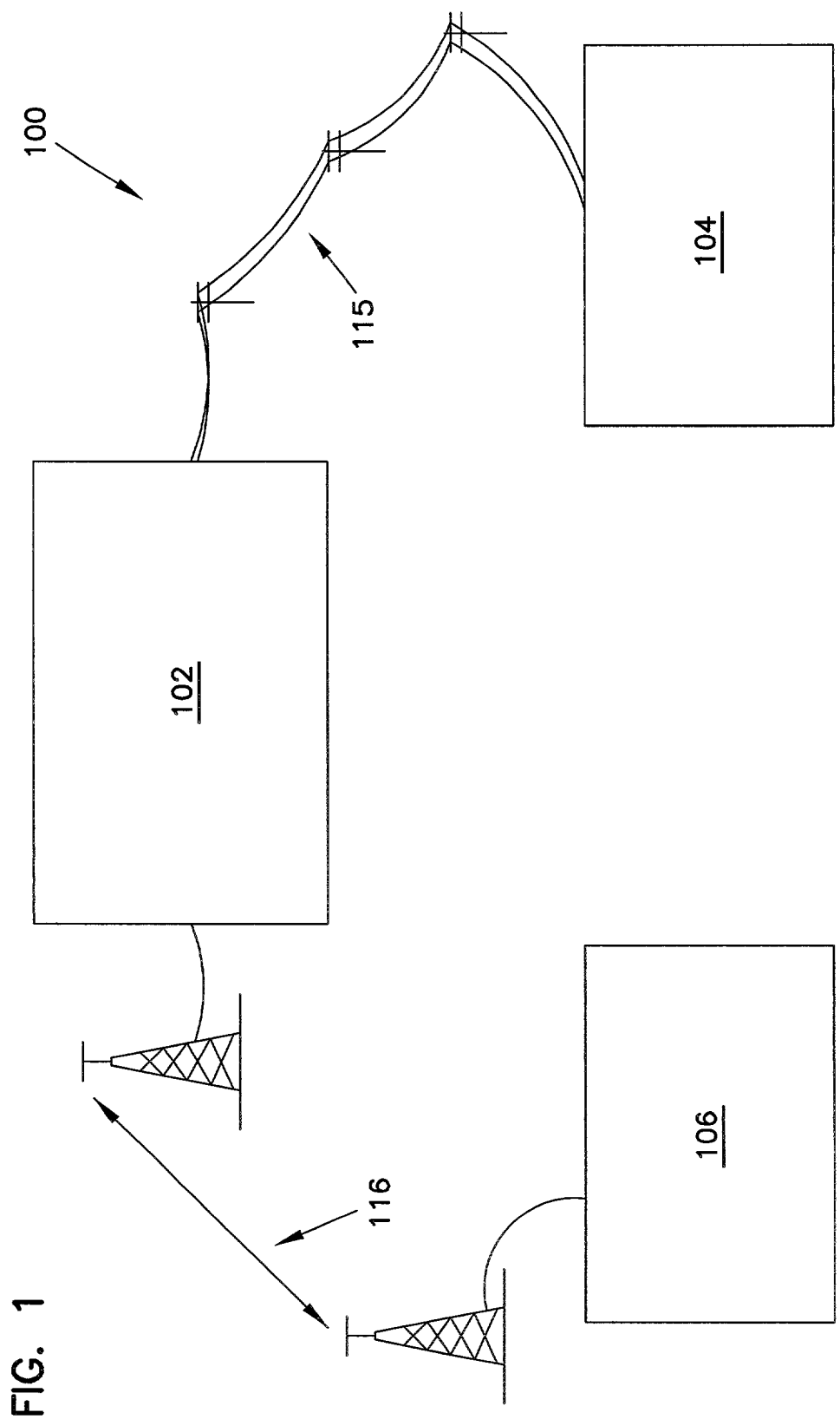
FIG. 1 illustrates an operational environment for a laboratory information management system in accordance with the present invention.
Figure 2:
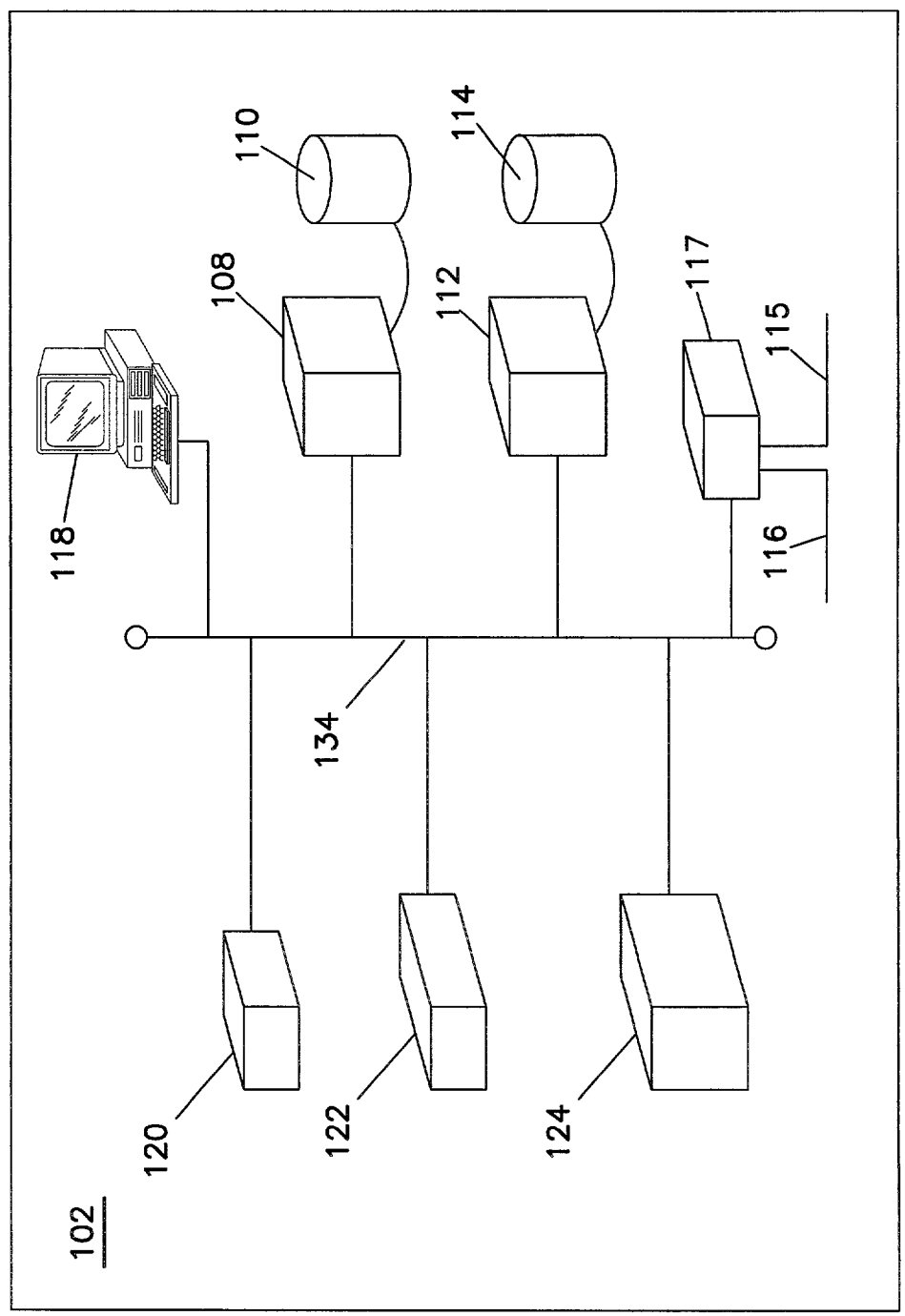
FIG. 2 illustrates an operational environment for a central installation of a laboratory information management system in accordance with the present invention.
Figure 3:
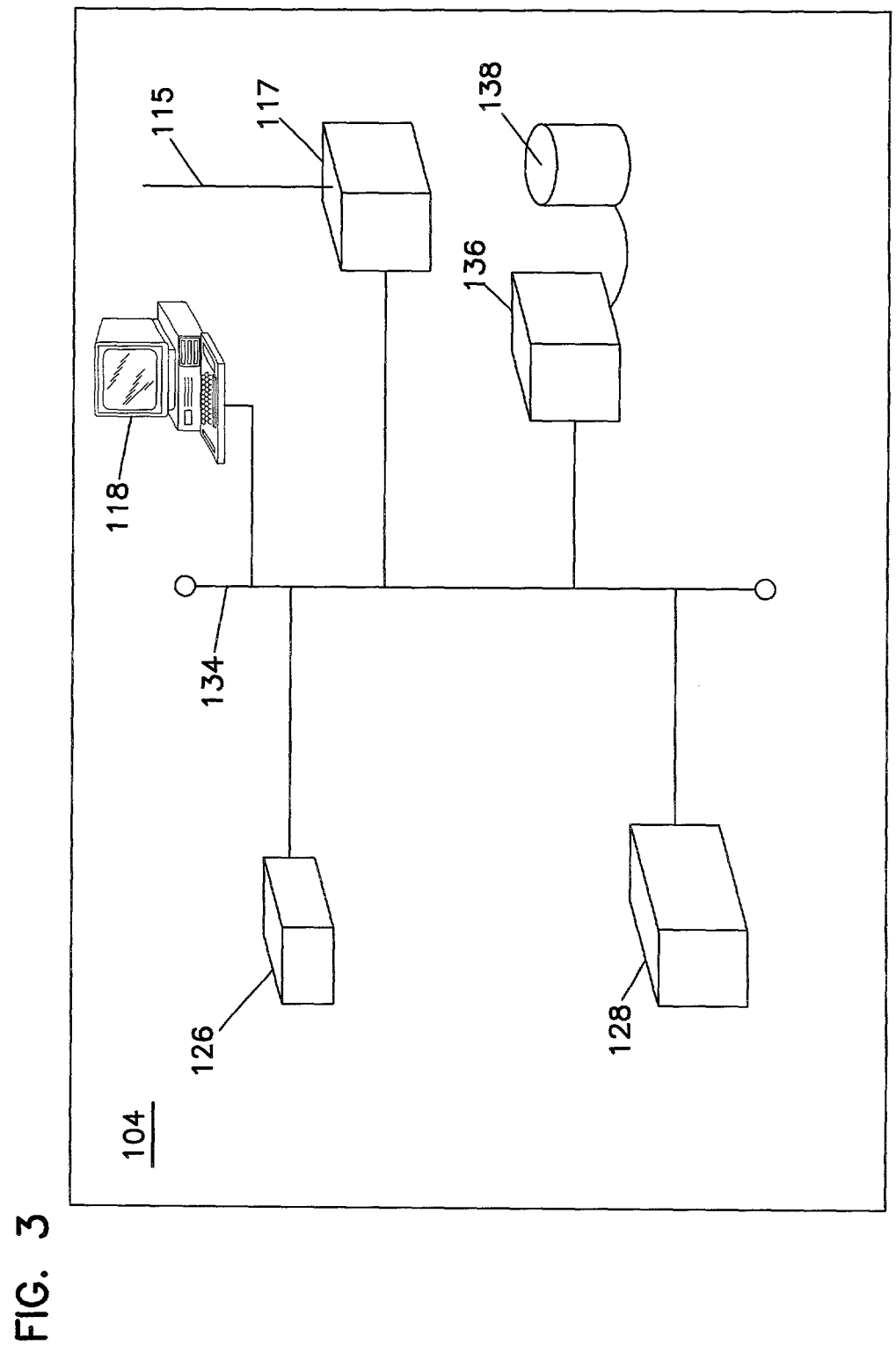
FIG. 3 illustrates an operational environment for a remote installation of a laboratory information management system in accordance with the present invention, the remote installation being linked to the central installation of FIG. 2 via a wired connection.
Figure 4:
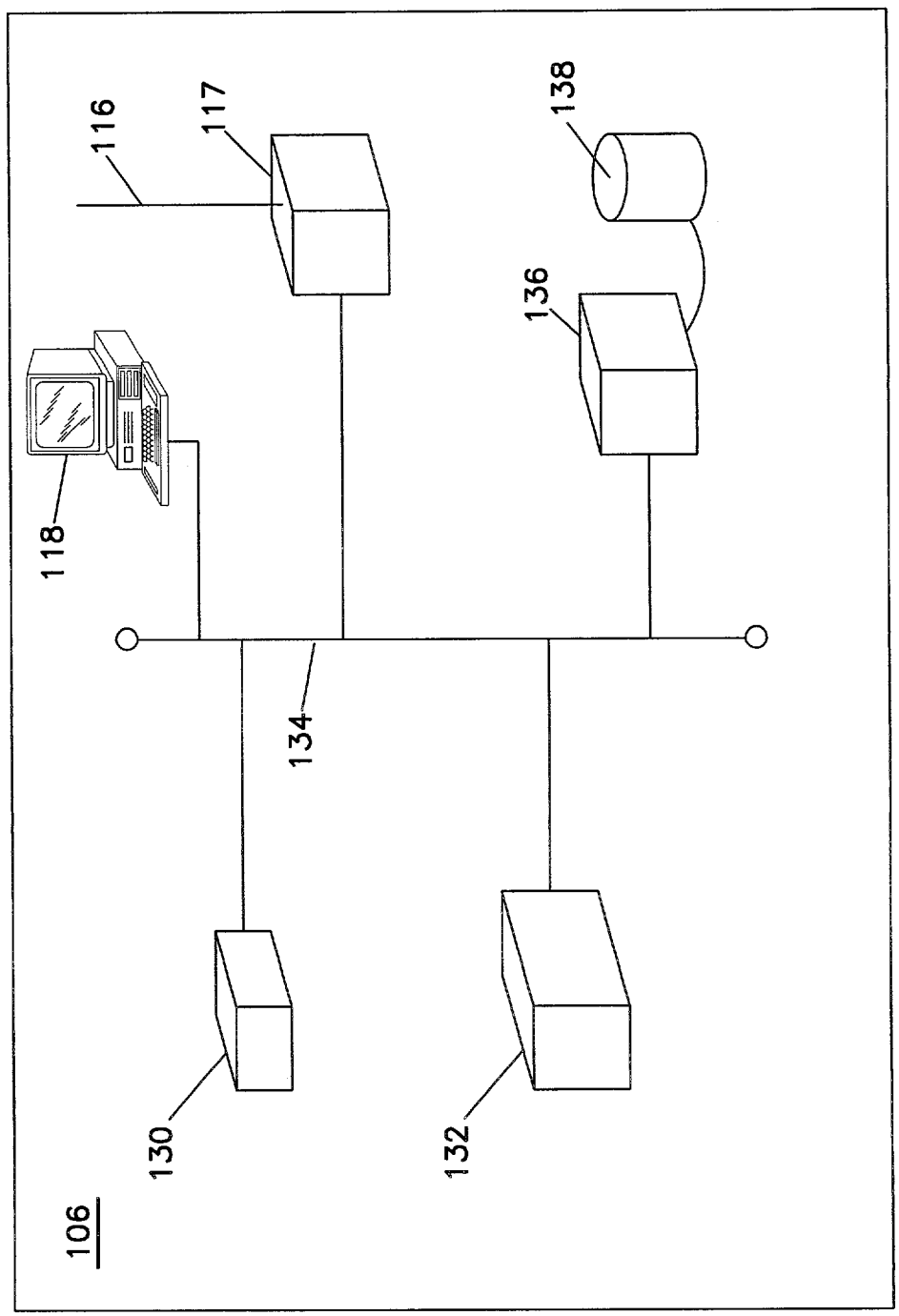
FIG. 4 illustrates an operational environment for a remote installation of a laboratory information management system in accordance with the present invention, the remote installation being linked to the central installation of FIG. 2 via a wireless connection.

The present invention discloses a multifunctional information management system that integrates a plurality of modules, each of the modules being interfaced via a relational database. The integrated system manages a large volume of business, data, and image information and is capable of being accessed/organized via the Internet.

As an example, the present invention provides an integrated ultrasound laboratory information management system suitable for a medical cardiovascular ultrasound imaging and hemodynamic laboratory, or an echocardiographic or comparable medical laboratory environment. The system supports patient management, data collection, and final report preparation and has the flexibility to support scaleable input of data from multiple sources. The system is dynamic and can easily be enhanced to grow with a laboratory's capacity and configuration. A final report of the system supports graphics that are accessed via an Internet web browser operating system.

The ultrasound laboratory information management system in accordance with the principles of the present invention is integrated mainly from three parts: a business management part, an ultrasound data management part, and an ultrasound image management part. The integrated system is capable of being used for a medical cardiovascular ultrasound imaging and hemodynamic laboratory (i.e., echocardiographic or comparable medical laboratory environment). In one embodiment, the integrated system includes a plurality of modules: 1) Scheduling and Workflow Module; 2) Patient Information and Demographics Module; 3) Billing Module; 4) Procedure Information and Referral Diagnosis Module; and 5) Measurement, Template, and Calculation Module; 6) Final Impression and Interpretation Module; 7) Procedure Report Module; 8) Serial Study Module; 9) Research Protocol Module; 10) User Interface and Service Module; 11) Web Based Module; 12) Unique Reports Module; 13) Database Module; 14) Systems Administration Module; 15) Security and User Conation Module; 16) Image Module; 17) System and Technical Support Module; and 18) Knowledge Base Module.

The advantages of the present invention are that the system is robust, template-driven, and Internet-accessible. The system has increased its reporting functionalities and provides guided billing functionality. In addition, the system provides outreach practice support and allows serial study of the measured data and information. Further, the system encompasses business management, data management, and image management.

The above-described modules of the system are described in detail as follows:

1) Scheduling and Workflow Module

The scheduling and workflow module of the system tracks a patient from initial scheduling of an appointment, through checkin, procedure, and checkout, i.e., discharge. The module may also contain the requirements for physicians, sonographers, and support staff to review workflow or workloops. It is appreciated that the system may receive information from other scheduling systems with an appropriate interface.

The operation of the scheduling and workflow module starts with a patient arriving at a specific echocardiography lab location for a procedure. The patient's visit is completed when the patient is discharged. There is a possibility that a patient may have more than one visit in a day, and that each visit may have multiple procedures scheduled. There may also be emergency situations where all the information needed to "check-in" a patient may be added later.

One step of the operation is to identify a patient's schedule on a given visit/day. This can be by a patient name, identification number, or other relevant information such as ID tag, time, lab location, referring physician, appointment type, and referral diagnosis, etc. Patient status, report status, assigned personnel, comments, and/or hospital information can then be viewed as they become available. The style of a scheduling display and/or variations of the scheduling display are dependent on the user's preference and may be used at the desk or checkin location for a lab.

Another step of the operation is to filter out certain viewed information from a scheduling display as a user may be only authorized to view certain information of the scheduling display. This filtering feature allows a user to readily change appointment dates and locations, appointment types, report status, patient status, and assigned personnel, etc. Further, a report filter allows one to look at all of the variables/fields or a combination of the available variables/fields. It is appreciated that additional report filter may be used to allow viewing all appointments or only filled appointments within the scope of the present invention, and that default views or templates may be configured by a user or a system administrator.

A further step of the operation is to provide a display that shows room status information at any point in time. The room status view illustrates that the data or information is arranged in such a way that it can be accessed by the other users, like viewing an "airport display board". In one embodiment, the display shows all rooms for a location. If a patient's record reflects "Roomed" or "Waiting Review", then the patient is reflected on the display.

In the scheduling and workflow module, all data recorded may have system-generated time stamps, as a patient proceeds through the visit from arrival to discharge.

The patients' appointments can be made at a central appointment desk (CAD) system and communicated to the other modules of the system through an external interface. It is also appreciated that patients' appointments can be made remotely. When an appointment is made in a remote site, the appointment is sent to the system. The system then matches the location, time, and appointment type and fills in the appropriate slot on the scheduling and workflow module. If the system does not find an appropriate slot to fill the appointment, then the system forces to fill in the appointment on the schedule and flag the appointment as "a forced appointment".

Also, a scheduled appointment can be deleted via the system. It is appreciated that the scheduled appointment can be deleted via a separate or remote appointment system. Such deletion is communicated to the system to further modify the scheduling and workflow module.

An additional step of the operation is to capture patient status information, such as the beginning time, current state, etc., throughout the visit. The step may also capture report status information, such as the beginning time, current state, etc., throughout the visit.

The changes made in the system can be automatically triggered or manually triggered, appointments can be made for any appointment type, and the module includes a flexibility to override most of the predefined fields. It is also appreciated that all appointments within a user specified time frame for an individual patient can be viewed. It is further appreciated that the scheduling and workflow module has the capability of moving appointments around and the capability of searching for appointments by person, referring physician, date, time, and status. Furthermore, it is appreciated that the scheduling and workflow module has the capability of searching for open appointments by a date range, location, and an appointment type. If a specific personnel is requested, the scheduling and workflow module may assign the personnel at the scheduling time. The schedule display highlights any specific personnel assigned to a patient that the status of the patient is less than roomed.

The scheduling and workflow module allows to identify sonographers, ECG tech and Echo staff availability by location. This can be accomplished by "check in" and "check out" statuses that are changed on the display. The scheduling and workflow module may also provide capability to view and monitor the unfilled capacity by location, appointment type, date, and day of week, etc. For example, the module creates an assignment list of available sonographers, physicians, and additional personnel as needed. This list is used to assign a specific personnel to a patient at check-in or at any other time during a medical procedure. Also, a patient status is changed manually by a system user or automatically, when applicable. Each change in status may create a system-generated time stamp. Thus, the module provides a dynamic display of patient status information, distinguishes in-patients from outpatients, allows to cancel a scheduled visit and make available history of cancel or rescheduled appointments, provides views for cancelled or rescheduled appointments, and allows the patient data to be searchable by a clinic number or patient number.

Also, the module provides capability of checking a patient's status on an individual basis and any available details, such as timestamp, length of time in status. For example, the module may provide the "No Show" review list and/or "Master Review List" by day and the ability to change their status on the display. The default view may looks like "Scheduled/Check In" view but in addition contains appointment date. The display may contain only patients with a report status of "Open" through "Report Complete". The patients remain on this list until they are in their final status. Filtering is available for all other statuses except scheduled, canceled, no show, and final. Accordingly, the module allows for a "Review List" but filtered by personnel. The default for the "Review List" may be all available report statuses and a logon user. A filter is established for users of the system so they only view certain locations/status of patients.

The module also monitors and assigns equipment available for lab usage. An equipment list is provided for such function. In one embodiment, a table is established to associate rooms with equipment so when rooms are assigned to patients, the equipment assignment takes place automatically. This equipment, by serial number and other identifier, would be kept with a record in the module. Accordingly, the module displays a location for each equipment. For example, if an electronic environment device (EED) is located outside a group of rooms, the module would provide default views of the patient studies currently in progress in these rooms. The module also provides capability for lab status view. For example, the module monitors, at any point during the day, a status of patients waiting, scheduled, or completed.

2) Patient Information and Demographics Module

The patient information and demographics module of the system is incorporated into the process of checking a patient in. It also includes demographic data and coordinates where that type of information is used or displayed. Some of this information is also described in the description of the scheduling and workflow module, above.

In an operation, as soon as a patient's visit begins, data are accumulated specific to the patient and procedure. Some of the data are available from an external system, such as a central review device (CRD). Additional data are recorded on the patient through the visit duration. An example of this data is hemodynamics, such as blood pressure, weight, height, etc.

The operation continues with accumulating/recording patient's registration and check-in information. The information collected at check-in is, for example, height, weight, BSA, BMI, birth date, sex, gestation age (if applicable), and fasting information, etc. Some of the information may be pre-loaded from the system through a user interface. When patient check-in is complete, a time stamp is taken, and the patient status is changed to "Check In". The patient information and demographics module keeps track of all item changed in a "change log" and shows demographic data on multiple views. For example, in outreach, the patient information and demographics module provides a place to input maiden name and previous married names of a patient, additional comments, etc. Based on the information in the module, a quick navigation to access information from a schedule can be made. It is appreciated that demographic data collection views may be different for outreach than in a central lab.

3) Billing Module

The billing module of the system accumulates and sends information to a remote billing system.

In an operation, for each procedure performed, the billing module captures all billable components and associates all billable entries with a specific patient, diagnosis, visit, and ordering physician. For example, the billing module creates an association between billing diagnoses and billing entries. This association validates that appropriate items are charged for the procedure. For all professional services provided, the billing module allows for the distinction between different classifications of procedures and the respective billing rates. Examples may include the classifications of "limited", "no charge", "complex", "grant", and "research account", etc. Accordingly, the billing module provides a unique list of billing items for each distinct billing classification of procedures and provides a reporting mechanism that communicates when procedures are completed but a billing record has not yet been sent.

Also, the billing module provides a monthly/daily summary of billing charges organized by day, site, and type of charge, procedure type. In one example, the billing module may provide a report of accounts of patients who have completed the procedure. In another example, the billing module provides a summary of charges year-to-date (YTD). Further, the billing module provides a clue of billing items, referral diagnoses, measurement performed, procedure type, and procedure components, etc. It is appreciated that the billing items, referral diagnoses, measurement performed, procedure type, and procedure components, can be coded or barcoded for searching and other functions.

4) Procedure Information and Referral Diagnoses Module

A procedure or study is the primary designation for the various activities surrounding a patient visit. A lab may perform multiple distinct procedures encompassing, for example, the gamut from pediatric to stress echo to intraoperative procedures. A physician referral diagnosis is provided whenever an appointment is created. It is generally a text that gives one as much information as possible about the reason the patient is scheduled for a study. The module may replace the text by a "coded" referral diagnosis. The "coded" referral diagnosis is determined by a sonographer early in a patient visit. This diagnosis then appears on a final report and is used for any retrospective retrieval. Billing referral diagnoses can be suggested based on the "coded" referral diagnoses. Also, billing referral diagnoses can be designated at the end of the patient visit based on the procedures performed, equipment used, and other practice-related factors. These diagnoses correspond to valid charge codes on the billing system.

As an example, when a patient is roomed, the system assigns personnel if not already assigned. This allows for easy navigation to assign personnel whenever they are available and allows for assignment of roles to a study when a specific individual is not known.

Also, procedure types are assigned to each study. The procedure types can be defaulted initially by an appointment type. For example, an appointment type of "EXERCI" stands for the procedure type of "Exercise Stress". By selecting an appropriate procedure type, the module uses this information to guide one to the best templates and tabs available in the system. For example, if a procedure type choice is transesophageal echo, then a tab is available to collect sedation information.

It is appreciated that some procedure types need further sub-division in order to guide a user to appropriate templates. An example of this is Exercise Stress procedure type. An Exercise Stress procedure type can be further divided into treadmill, bicycle, and interpretation only.

Procedure types are also associated with procedure components. Procedure components are descriptions of what is actually done during a study. For example, the procedure type of basic adult echo generates procedure components of 2D, Mmode, and Color Doppler, etc. There is still an outstanding issue of whether the procedure components are needed for a final report. The system also allows multiple procedure components to be selected and assigned during a single visit if needed. The system determines initial required medical history information based on referring diagnoses and procedure component and supports the use of templates for organizing measurements into predefined groups. Accordingly, the system allows the ability to select or use any template. The system can also determine the initial required medical history information based on referring diagnosis and procedure type.

In operating the Procedure Information and Referral Diagnoses Module, time stamps are collected during a procedure that records check-in, roomed, and discharge times, and preliminary impressions or other comments are recorded from sonographers and other clinicians throughout the patient visit whenever needed. The user may designate which of these should appear on a procedure report. Clinician comments and dictated physician comments should be optionally checked for spelling errors.

As an example, an appointment type of "Research XXX" indicates that this is for a specific set of procedure types. Once this is chosen, very specific templates for the studies can be selected. Research templates must have every data item as a required field. This is different from other study templates. Based on this, a requirement of the templates is to vary whether fields are required or optional.

Also, based on the capabilities of the measurement and calculation database, there may be an additional need to store specific "stress" information outside of the configurable database. Different protocols may require different templates and different data items.

The module also provides access to sedation template for any procedure type that may require sedation. Data items needed for printed report are a subset of the standard data recorded on all patients, plus significant other data. A lot of this data is a free form text that does not easily fit into the measurement database.

5) Measurements, Templates, and Calculations Module

Measurements are the core data components that provide the ability to effectively diagnose patient health. A lab, such as an echo lab, operates in a dynamic environment due to advances in medical knowledge and diagnostic instrument capabilities. The present system has the ability to define new measurements and incorporate them into procedures. With the number of measurements and calculation possibilities, it is important to be able to dynamically organize data items according to the type of study being performed. The use of templates (pre-organized data) facilitates the quickest data entry possible. The system also organizes the data for analysis that may be different than the organization necessary for input. Templates facilitate this as well. The module allows the definition of custom numeric measurements and depends on the configurable numeric measurements for all procedure measurement data acquisition. These measurements include echo-specific and other clinical measurements. Each measurement may ask for sufficient information to describe the data type and precision, anatomical section, valid modalities, display and symbolic labels, units of measure, timing, and measurement name/type. Some notion of versioning may be required to ensure proper interpretation and retrospective aggregation of "modified" measurements.

The module also allows the definition of qualitative measurements. Qualitative measurements provide the ability to make subjective assessments or general comments regarding a particular anatomical area or other miscellaneous procedure aspect. The most basic type of qualitative measurement is a free form text string. Other qualitative measurements may make use of selection lists. This latter type may be used in calculated measurement expressions, primarily as the test condition in "If" tests.

Further, the module allows the definition and validation of calculated measurements. Calculated measurements are the product of previously defined numerical measurements, constants, and logic selection based on selection list-based qualitative measurements. Formulas are created using the measurement symbolic names and mathematical operators. Certain patient/visit attributes, such as height and weight, need to be available to a calculation engine. Editing any entered measurements result in re-computation of a calculated result. Descriptions of measurements may be available via a help function key. Descriptive information may also include externally created text as well as a symbolic representation of calculations used for calculated measurements. The module allows the definition of measurement templates to facilitate date entry. Measurement template also allows the user to organize measurements into groups based on anatomy, modality, or other paradigms chosen by the lab. For example, a stress protocol template can be included for capturing time-series measurement values. Stress protocols identify predetermined control variables applied and measurements collected overtime during a stress procedure. In an exercise stress echo, a treadmill grade and speed are control variables, while heart rate and blood pressure are acquired measurements. In a pharmacological stress procedure, medication and dosage may replace grade and speed. The protocol also defines the time interval (or possibly another event) between stages.

The module also supports the creation of predefined stress protocols that provide the stages or steps of stress echo procedures. Typically, this involves specifying the "control variables" and time intervals. Automatically generated procedure measurement entry screens are based on template content. Templates may require additional information to help in screen layout. Such information may include grouping indicators and orientation. The order of measurements in a template helps determine ordering on the entry screens. An example would be a stenosis indicator on a template that, when pushed, would change the template or template content.

The module further supports capability of report templates. These templates are used to produce a framework or roadmap for a report, e.g. an Echo report. The template supplies the interpretation requirements and measurements. Additional items can be added adhoc to the echo report as it is being built.

In addition, the module supports the storage, retrieval, and calculations of normal ranges for measurements. Normals result from data collection and analysis over time. Demographic categorization is the primary method of differentiating normals across a population. For example, all males over 20 may share normals for a particular set of measurements. The approach to implementing normals supports the ability to stratify a patient and return values from database tables and/or calculations, and to add new tables and algorithms for normals computation and lookup without modifying the primary application.

As research proceeds or new prosthetic devices are brought to market, the need arises to extend the existing normals models. The present system provides a solution by creating normals models and returning values that are independent or well abstracted from the primary application. The system may utilize the following tables: Feignbaum tables for adults without BSA measurement; Gardin tables for adults with BSA measurement; Henry tables for pediatric patients; Prosthetic valve normal ranges—from manufacturer; and Diastolic function normal ranges. The module allows to visually flag any measurements falling outside normal ranges and provides ability to organize measurements by normals and those outside the normal range.

Furthermore, the module provides ability/extensibility to dynamically build templates based on an image and measurements recorded on the image. A specific measurement is only required to be input once, regardless of any change in templates, procedure type, or hemodynamic data. The system also accommodates enhancements necessary for future association of measurements to data acquired from multi-vendor ultrasound equipment via interfaces, such as the Digital Imaging and Communications in Medicine (DICOM) interface. The measurements accept more than one input value, resulting in an average for the measurement. The system stores and displays all entered data and allow them to be reedited, resulting in a re-computation of the average. An averaged result can be flagged visually on entry screens and reports.

Moreover, measurements are retrievable via a relational database query tools. Due to the desire for a measurement system to be configurable, the database tables used for storing measurements may not conform with the traditional notion of a database field corresponding to each measurement. Rather, a name/value approach is used, which would require intermediate processing in order to create optimal tables and queries for research purposes. Such intermediate processing may probably occur after hours, which in turn would minimize performance impact of queries on a production database. Measurement entry and storage allow for entering multiple sets of measurements at user-defined points during the procedures.

Procedures, such as respiratory comparisons, require that two or more sets of measurements be obtained. The module provides default stages for these procedure types, such as prestress/poststress, as well as allowing for new measurement sets to be created and labeled as needed.

The module also supports a graphic-based annotation method for wall motion data interpretation and scoring. The graphic display may include multiple cross-sectional views. The views may include peristernal short axis, apical 4 chamber; apical long axis; apical 2 chamber; and peristernal long axis.

The module may also support a graphic-based annotation method for thoracic aorta measurements. The data generated from the measurements supports a thoracic aorta serial study.

6) Final Impressions and Interpretations Module

The interpretation of a clinical patient visit is summarized via final impressions. Physicians create final impressions to communicate clinical assessments and recommendations to the patient and other caregivers associated with the patient's current and ongoing care and treatment. The physician final impressions are an important component of a patient's report, such as an echo report. Sonographers create independent "coded" final impressions to aid in retrospective retrieval of studies based on standardized phrases and terms. These coded final impressions are not included in the procedure report. The final impressions and interpretations module provides a free form comment area that the consultant or sonographer can dictate or type comments that are significant about the study that cannot be captured easily by the final impression statements.

In the measurement capture and analysis templates, the module provides ability to access final impressions statements. This requires that specific templates or measurements have a logical relationship to final impression statements. For example, an ejection fraction measurement may have a statement that states an observation about the ejection fraction and puts in the measurement result into the statement. Another statement may require that a measurement be recognized as normal and automatically generate a statement that describes normal function.

Different procedure types display different report templates. These report templates have categories of statements that must be coded in order for the report to be complete. They help facilitate completeness and consistency. These coded statements generate text or bullet items for an interpretation section of the report, e.g. an echo report. In addition, these coded statements are used for retrospective studies.

The report interpretation section can be dynamically generated by the measurements, sonographer coding, and/or consultant coding. The module allows to extract or mark any coded item to be also shown as a final impression. A coding mechanism may be required to allow the assembly of final impression phrases with corresponding numeric representations that may be accessed for retrospective research via relational database access. The module also has the capabilities which include prompted numeric values and ranges, singular/plural modifiers, test substitution, ordered parameters, modifiers, report or entry form suppression, free-form text entry, date/time prompting, and linking of phrases into paragraphs, etc.

7) Procedure Report Module

As soon as a patient is checked in, data becomes available that makes up the patient visit report. There are two primary "views" of the visit data from a reporting standpoint. The "Procedure Log" contains all data collected during a visit. The "Procedure Report" contains the sections of the "Procedure Log" that are considered important to the patient and clinical clients of the lab.

Until the procedure report has been approved by the assigned physician, it is considered a preliminary report. At specific stages during the visit (and the life time of a report), a version of this report is sent to a system, e.g. ERIS system. A copy of the final report is placed in the patient history folder. All data applying to a patient visit is organized by sections to facilitate assembly and customization of the procedure log and report. Examples of the a report sections may include Demographics; Referring Diagnosis; Hemodynamics; Doppler Measurements; Stress Parameters; and Wall Motion Graphics, etc.

The report module also allows default inclusion/exclusion and ordering of data sections for multiple versions of the report. Report versions may include Online procedure Log; Online procedure report; Printed procedure report; and ERIS procedure report, etc. The report module also specifies ad hoc inclusion/exclusion of data sections for a specific report version applied to a particular visit.

In a reporting process, typically a report signoff sequence requires sonographer signoff prior to physician signoff. In the present system, the physicians and sonographers may perform report signoffs from remote locations via Web access. During an online report review, specific signoffs may be authorized and performed by required clinician regardless of whether a current user logged into the system. In the report module, customized versions of a preliminary or final report can be sent to an electronic report system based on either specific data modifications or specific patient visit status transitions or events. This allows efficient navigation to and from data sources from the online report. Further, access to data element helps text and calculation definition from the online report. Also, an immediately update report data based on changes to underlying visit data can be generated.

Further, the report module may incorporate all graphic elements of data, for example, wall motion graphics, thoracic aorta view, on devices with a graphic display capability. The report may also provide an alternate textual representation of graphically generated data, for example, wall motion comments/scoring, to be used for output targets without a graphic display capability. The final reports may be faxed to outreach or other remote locations. Any data modifications subsequent to a final report signoff may result in future reports indicating that the report has been modified. Modified data may be optionally flagged in an online report.

It is appreciated that an online report is optional, and that the report can be a printed report. The module may use distinct, easily seen graphical cues online and printed reports to distinguish between preliminary and final reports, and between original and modified final reports.

8) Serial Studies Module

Serial studies allow for the time-based analysis of particular measurements regarding a specific patient. They are typically used for tracking the progress and health of a particular patient. In contrast, research studies or protocols aggregate measurements from many patients for the purpose of statistical analysis.

Serial studies are identified and created by study type. Serial study types may include oncological and hypertensive types. Each patient may only have one serial study of each type active at a given time. Additional serial study types can be created at any time. Serial studies may be initiated for a patient at any time. The incorporation of a particular visit into an ongoing serial study may be at the discretion of the clinicians.

It is appreciated that in some instances, a particular visit may not be flagged, as the visit is not applicable to a serial study so as not to skew trend data or due to emergency procedures. By default, a visit may become a part of a serial study, but a user may override the default.

Once a measurement has been assigned to a particular study type, the module may prompt or otherwise aid the user in acquiring the measurement in future studies. The serial studies module provides the ability to review the measurements assigned to serial studies across all applicable visits. Data are displayed in a convenient format, such as a tabular format. Individual measurements should be selectable for graphic representation and/or comparison over time. Serial studies may be included on a procedure log and/or a procedure report as desired.

9) Research Protocols Module

Research protocols module provides retrospective statistical analysis of aggregated patient data to support the research and educational needs of a practice and other organizations. Data for research protocols module may include measurements, demographics, and/or other subjective information. Research can be partitioned for clinical information in order to accommodate rules of privacy.

Unique billing codes may be assigned to research protocols. The module may prompt or otherwise aid a user in identifying missing protocol measurements since it may be preferred that all measurements assigned to a protocol are collected during a protocol visit. It is appreciated that a visit may be scheduled in support of multiple protocols. The data associated with a protocol are provided to researchers by the research protocols module or any other modules in the system.

The module allows the creation of research protocol definitions at any time and allows measurements to be assigned to research protocols. Also, the module accommodates the creation of questionnaire-style informational data items that can be quantified or stratified for research purposes.

10) User Interface and Common Services Module

The user interface and common services module provides both automatic and user-initiated mechanism for storing data. The module provides an "expert mode" support for rapid entry of data to familiar users. The module thus allows efficient, intuitive navigation to all components of a patient visit. It is appreciated that the automatic data storing mechanism or user-initiated data storing mechanism can be any known type, such as the computer software wizards or templates, etc. It is also appreciated that the user interface and common services module can be operated in the Internet environment.

11) Web-Based Module

The web-based module provides all application interface screens primarily deployed within a web browser. The security feature is implemented in the web-based module to restrict certain operational interface access, for example, measurement entry, scheduling, etc., to the appropriate departmental or institutional personnel. The security implementation allows for viewing of a report, such as a patient's final report, by a variety of interested parties, especially referring physicians. The security features can be configured in a separate module, such as a security and user configuration module (see later discussion).

Accordingly, the system can be web-based. The system may be implemented by using a combination of XML, dynamic HTML, static HTML, Java, or an Oracle database, etc. The technologies simplify deployment by allowing the application to be deployed in a web browser. For example, by using Enterprise Java Beans, the system may generate an XML report that can be stored in a database allowing for easy access from any electronic medical system.

In one exemplary implementation, the system may incorporate the following applications:

At the server side technology:
  Java and EJB (server-side component architecture, rapid application development, maintainability and extensibility),
  Database and XML (dynamic document-oriented view of visit and measurements, portable data format, XML-to-relational mapping of reports), or
  Sun-Oracle-BEA's WebLogic (scaleable, reliable, secure);

At the client side technologies:
  Java Applets ("List" oriented views, synchronization of data),
  DHTML (patient-centered views, frame management, Javascript for local validation where appropriate), or
  Sun-Oricle-BEA's WebLogic (track record, scaleable, reliable and secure).

12) Unique Reports Module

In addition to a procedure report, other reports may be generated to aid in various phases of user operations. Some of these reports are automatically generated based on specific system actions or visit statuses. Others can be generated upon request. Also, the module identifies which location or a remote location a report is sent to.

The module also provides a relational database with supporting views to allow effective creation of predefined and ad hoc practice management reports.

13) Database Module

The database module stores all application data in a relational database for ad hoc query and statistical analysis access. It is appreciated that any known relational database can be used without departing from the scope of the present invention.

14) System Administration Module

The system administration module configures a select list for selection fields/combo boxes not specifically populated from database contents or measurement configuration. It is appreciated that any known system manager functions may be used within the scope of the present invention.

15) Security and User Configuration Module

The security and user configuration module provides security functions for the system both internally and externally. For example, the module identifies particular users to access particular fields of the system according to defined users' roles in the system.

For example, identified users' roles may include sonographer, physician, appointment secretary, desk secretary, technician, and administrator, etc. It is appreciated that users may be added or deleted from a pre-defined user list. Accordingly, the module provides the capability to restrict access to application screens by lab role and individual user.

The implementation for the security access to the system can be any known mechanism, such as the traditional security access by login ID and password. The login ID and password mechanism can be separate or distinct from other applications operated on a system. Further, workstation locations can be pre-defined by the system at login, and defaults for initial screens, room coverage, and printer location can be pre-defined.

Medical information and patient privacy are heavily regulated in the United States and in foreign countries. The security and user configuration module are preferably compliant with the current known regimes of regulation in the country of implementation of the system, and are adaptable to meet new requirements and regulations as new regimes are enacted. In the U.S. at this time, the Health Information Patient Privacy Act (HIPPA) is the principal regulatory structure. The security and user configuration module is preferably compliant with and adaptable to meet all current and future HIPPA requirements.

16) Image Integration Module

The image integration module may be implemented in association with imaging systems, such as echocardiogram imaging systems, etc. Accordingly, the module is capable of adapting to the features and/or functions similar to the imaging systems. For example, the module stores image data from a patient study, measurements, demographic, and/or other relevant data available, on electronic media, such as DICOM-enabled ultrasound systems.

The image integration module also transfers demographic information from a lab system to another appropriate ultrasound device via DICOM prior to beginning of a study or when information is made available. This allows rapid random access to the stored image data that corresponds to a study.

In addition, the image integration module provides an enhanced user interface that includes measurement "tools" familiar to ultrasound users so that it allows measurements to be created or modified retrospectively.

Further, the image integration system may incorporate selected images and video segments into an online patient report at the discretion of users. It is appreciated that restrictions on delivery technologies, such as printers and electronic record system, may restrict the selected images and video segments on certain formats.

In cases where a single measurement is made multiple times, a user can either select a single instance or have the module to average selected values.

17) System/Technical Support Module

The system/technical support module supports separate test, integration, and production environments, provides on-line access to manuals covering user navigation and system overview, and/or provides a Technical Engineering Document. It is appreciated that the system/technical support module may adhere to certain guidelines, such as published system/technical user interface guidelines, a systems administrator guide, etc. Further, the module provides schedules for backup and system maintenance activities.

The module further provides a robust, automatic distribution, and installation feature. This feature allows easy dissemination of updated software to client hardware. When a workstation first accesses the system, the system ascertains whether a more up-to-date version of the software exists. If so, the system downloads and installs the up-to-date version before a user proceeds.

Furthermore, the module archives data based on user-specified aging parameters and provides a capability to retrieve archived data for query. For example, the module supports a data capacity based on patient visits for the number of patients in the first year, with the practice growing by a percentage per year thereafter. Another example is that the module supports a minimum 3-year on-line data capacity based on performing a number of procedures in the first year, with the practice growing by a percentage per year thereafter. A further example is that the module supports an installed base of 100 to 17,000 workstations, with 150 users logged on at a time, and allowing for 100 concurrent data entry users.

In one implementation, the system runs on WINDOW NT 4.0 with 32M of RAM, 133 to 300 Megahertz CPUs.

For enhanced system performance, activities taking place in the patient's presence are prioritized higher than administrative reporting activities. The module displays a warning when concurrent updates are attempted. Within each major task of a patient visit, the module expedites the processing of screens so as not to impede progress. The module is optimized for response time performance, once a patient has been selected and once task has been initiated.

In one implementation, the module supports maximum system response times of less than two seconds when moving between patient states, or when switching to a patient visit from history that is not cached. During a patient visit (either a current one or a past visit which has been loaded to cache), responses from a server to a client are within one half second. For all responses that rely on external interfaces, the response time is preferably less than two seconds. It is appreciated that other response time can be implemented within the scope of the invention.

18) Knowledge Base Module

In one implementation, the knowledge base can provide information to users of the system and clinicians as which tests should be performed or which measurements should be collected for a given initial diagnosis. Valid ranges for measurements or outcomes for particular procedures are provided to clinicians and technicians carrying out the test and measurements to ensure that valid data are collected. Once initial data has been collected during a patient visit, the knowledge base can provide the clinician feedback regarding the initial diagnosis and whether the data collected appears to support that diagnosis. If the data appear to suggest a different diagnosis, the knowledge base can prompt the clinician to perform additional measurements and gather additional information that may further confirm the initial diagnosis or point to a new diagnosis.

The knowledge base module may be developed from the collective background knowledge of the ultrasound laboratory derived from many years of operation. Statistical and other historical analysis of data and diagnosis of prior patient outcomes, in combination with the knowledge and expertise of current clinicians contribute to the knowledge base. As new ultrasound tools and techniques are incorporated into laboratory operations, initial assumptions as to appropriate valid measurement ranges are included in the knowledge base and verified against the actual measurements observed during clinical usage. Further, the initial and revised diagnoses supported by particular measurements derived from such new tools and techniques are also incorporated into the knowledge base. As more experience with the new tools and techniques are gained through clinical use, these initial assumptions may be tested against actual patient outcomes to revise and refine the contents of the knowledge base.

In another implementation of the knowledge base, the knowledge base incorporates a universal glossary related to the operation of an ultrasound laboratory. By supplying all users of the laboratory information management system with a common taxonomy, more uniform and consistent data regarding diagnoses, measurements and outcomes can be promoted, which will in turn allow the knowledge base to be maintained, improved and extended. To permit and promote this on-going improvement and extension of the knowledge base, users of the laboratory information management system may be required to agree to use of the common glossary when taking and compiling measurements.

Referring now to FIGS. 1 through 4, a sample operational environment for an ultrasound laboratory information management system 100 is illustrated. System 100 includes a central office or laboratory installation 102, and two remote laboratory installations 104 and 106. Installation 102 includes a module server 108 with an attached database 110, a knowledge base server 112 with an attached database 114, at least one client intake system 118 and multiple ultrasound devices 120, 122, and 124. Also included in installation 102 is a communications gateway 117. These elements which comprise installation 102 are linked by a local area network or LAN 134. It is anticipated that more ultrasound devices may be included in installation 102. In addition to ultrasound devices, other laboratory analysis tools may be incorporated into installation 102 and linked to the other elements of installation 102 via LAN 134. Module server 108 may include multiple physical servers or a single high-throughput server. Databases 110 and 114 can be logical partitions of a single database server or may be physically distinct database servers. In addition, each of the database servers 110 and 112 may include multiple physical servers. The size and number of hardware devices included in central laboratory installation 102 will depend on the size and overall complexity of installation 102, the number of users supported by installation 102, the number of ultrasound devices 120, 122 and 124 included in installation 102 and the capabilities of the hardware and software which comprise the installation.

Remote laboratory installations 104 and 106 are similarly configured to installation 102. It is anticipated that remote installations 104 and 106 will be smaller and support fewer users than installation 102. However, a remote installation 104 or 106 may actually be larger or more complex than installation 102. It is also anticipated that more or fewer remote installations may be incorporated into system 100.

Remote installation 104 includes a client intake system 118, a number of ultrasound devices 126 and 128 and a LAN 134. Remote installation 104 also includes a communication gateway 117 which is linked with communications gateway 117 of installation 102 via a wired connection 115, such as an intranet, the Internet, a leased line or a combination thereof.

Remote installation 104 may also include a local server 136 and local database 138 to capture and maintain data from patients seen at remote installation 104 which is only of interest to laboratory staff at remote location 104.

Remote installation 106 includes a client intake system 118, a number of ultrasound devices 130 and 132 and a LAN 134. Remote installation 106 also includes a communication gateway 117 which is linked with communications gateway 117 of installation 102 via a connection 116 which includes a wireless communication element such as satellite networking, cellular technology or radio communication. Remote installation 106 may also include a local server 136 and local database 138 to capture and maintain data from patients seen at remote installation 104 which is only of interest to laboratory staff at remote location 106.

It is anticipated that more ultrasound devices may be included in remote installations 104 and 106. In addition to ultrasound devices, other laboratory analysis tools may be incorporated into remote installations 104 and 106 and linked to the other elements of remote installations 104 and 106 via LANs 134.

Referring now to FIG. 5, an overall table layout 200 which supports the integrated laboratory information management system is shown. FIG. 5 indicates the individual grids into which table layout 200 has been broken down into and indicates which of the following FIGS. 5A through 5X includes a more detailed view of data tables and data linkages within the grids.

Figure 5A:
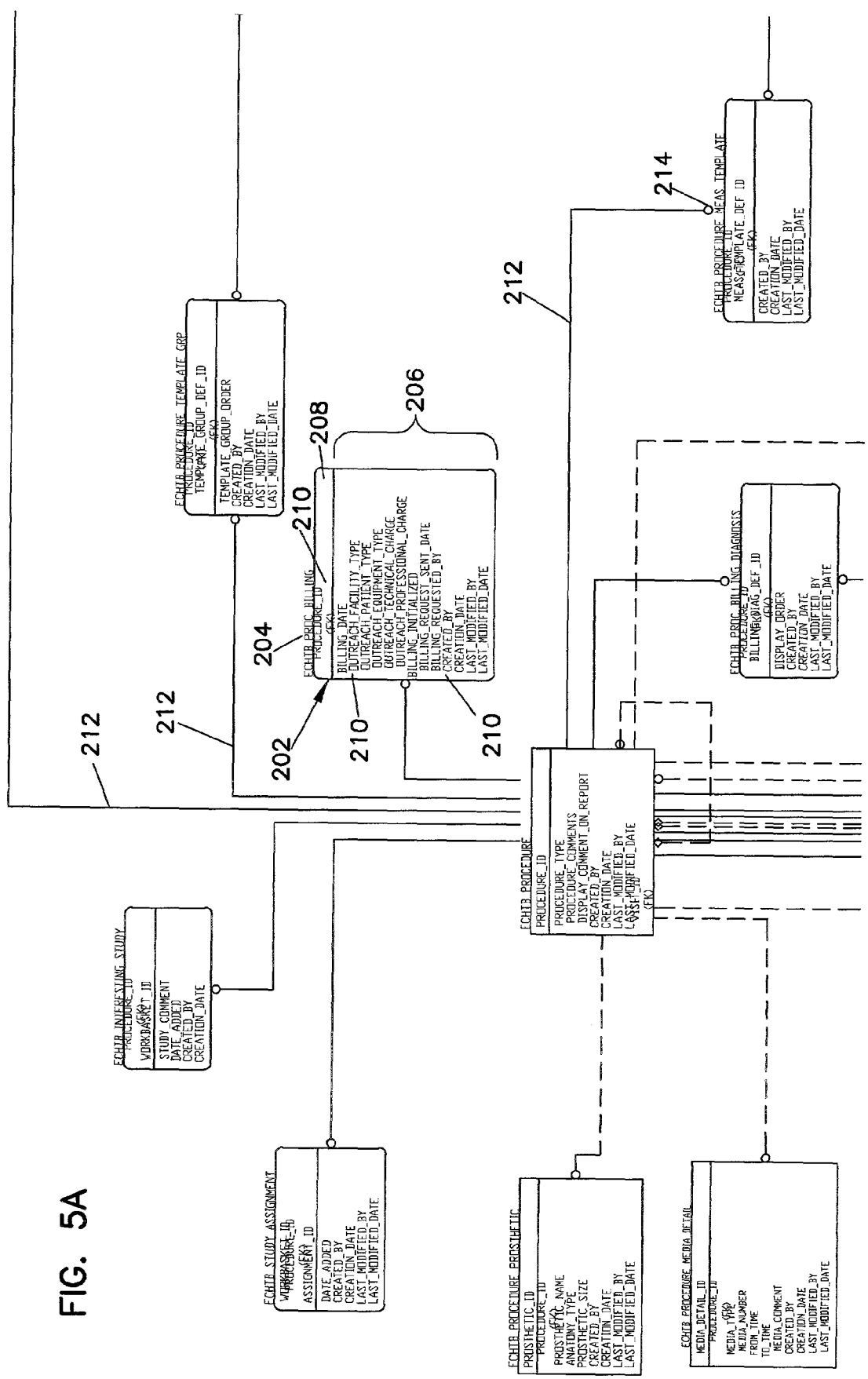
FIGS. 5 and 5A through 5X illustrate a database table diagram for a laboratory information management system in accordance with the principles of the present invention.
Figure 5B:
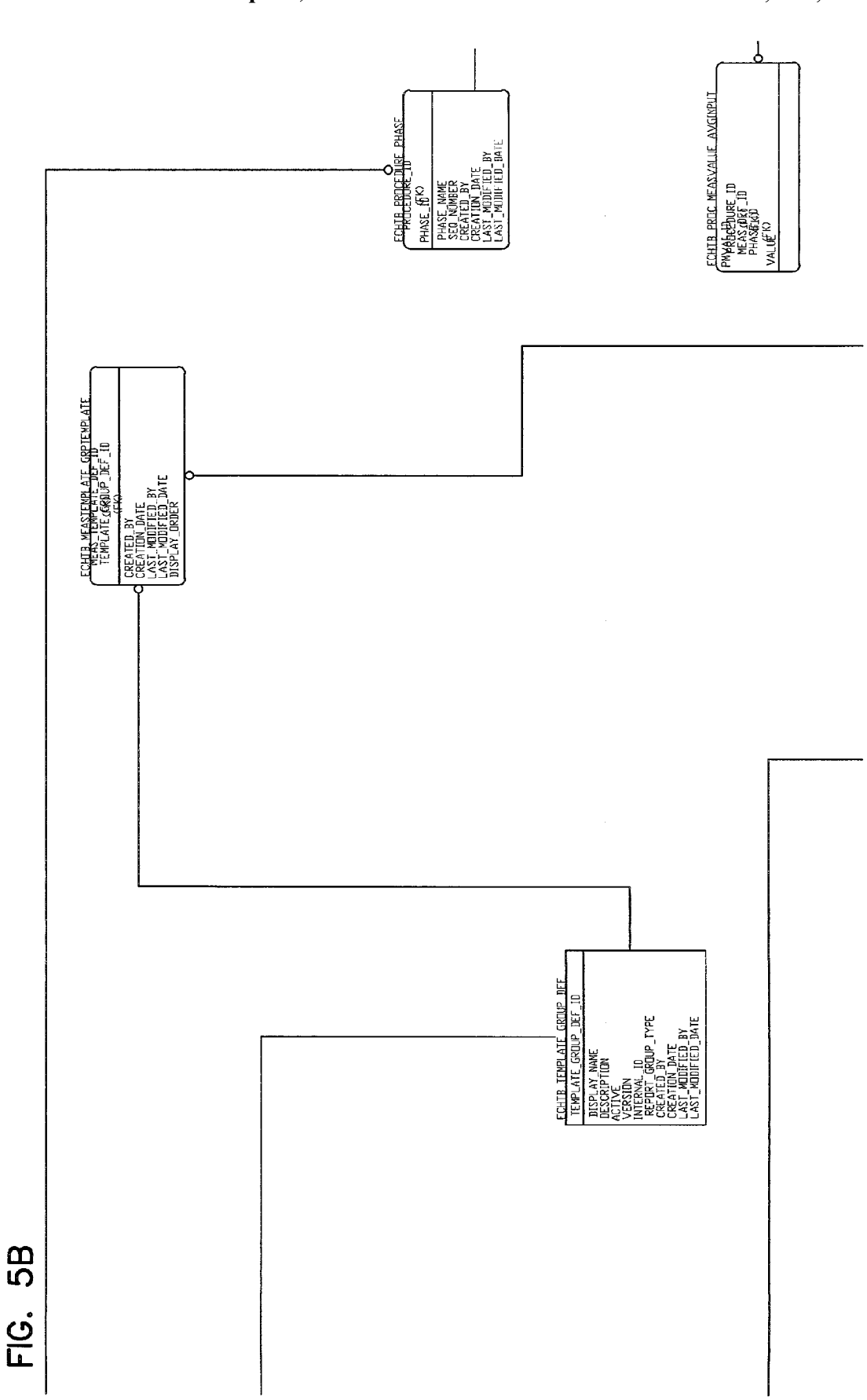
Figure 5C:
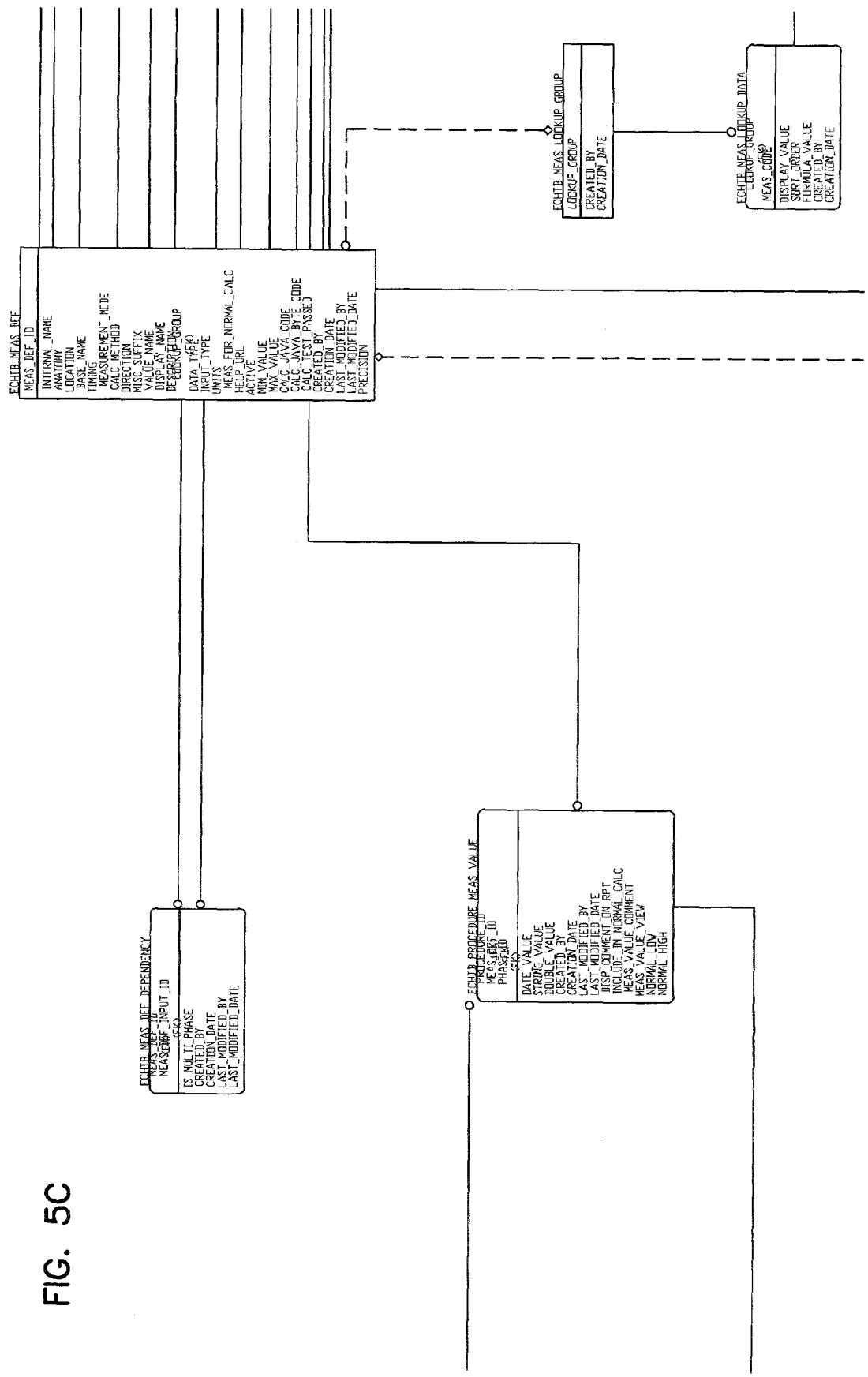
Figure 5D:
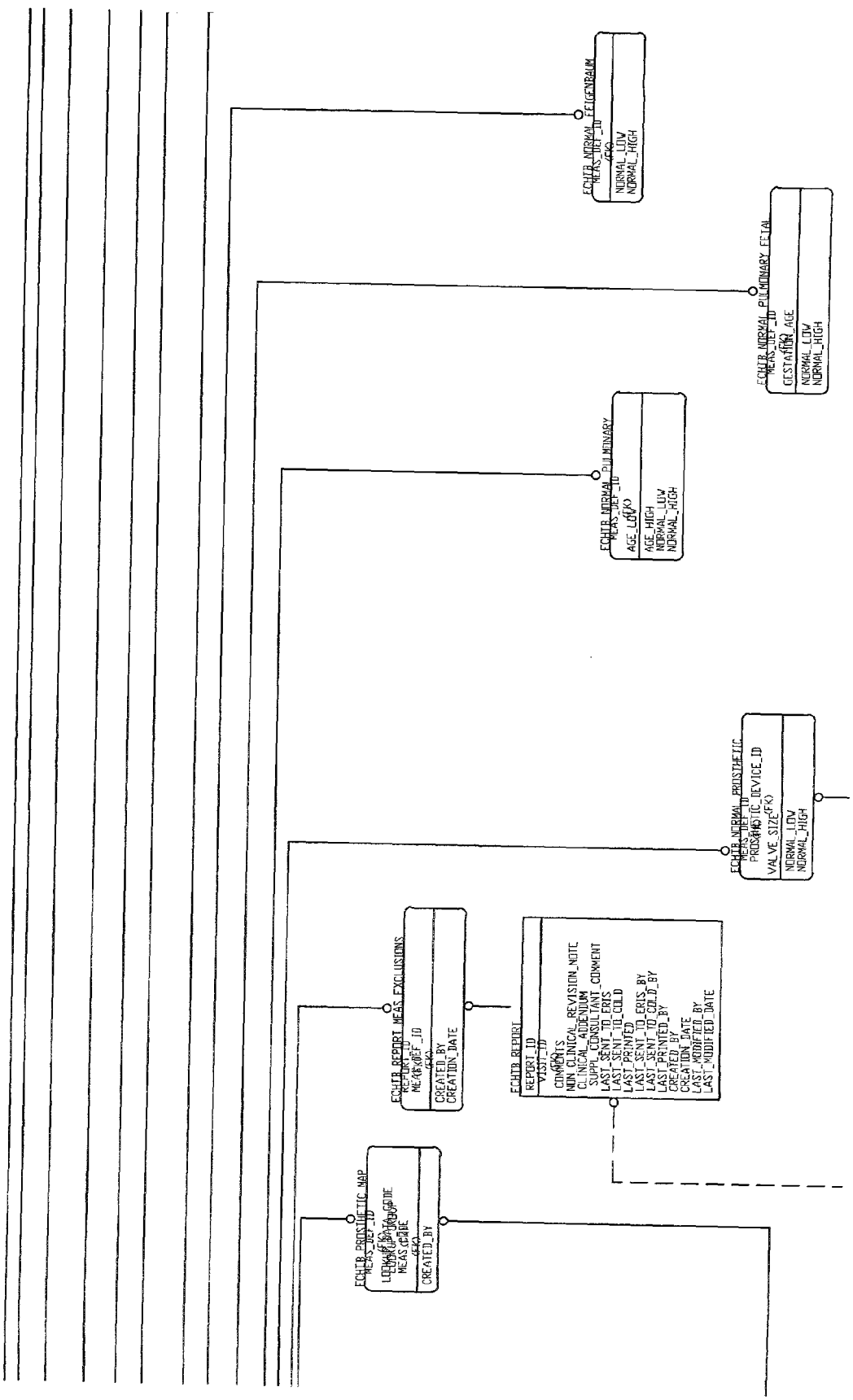
Figure 5E:
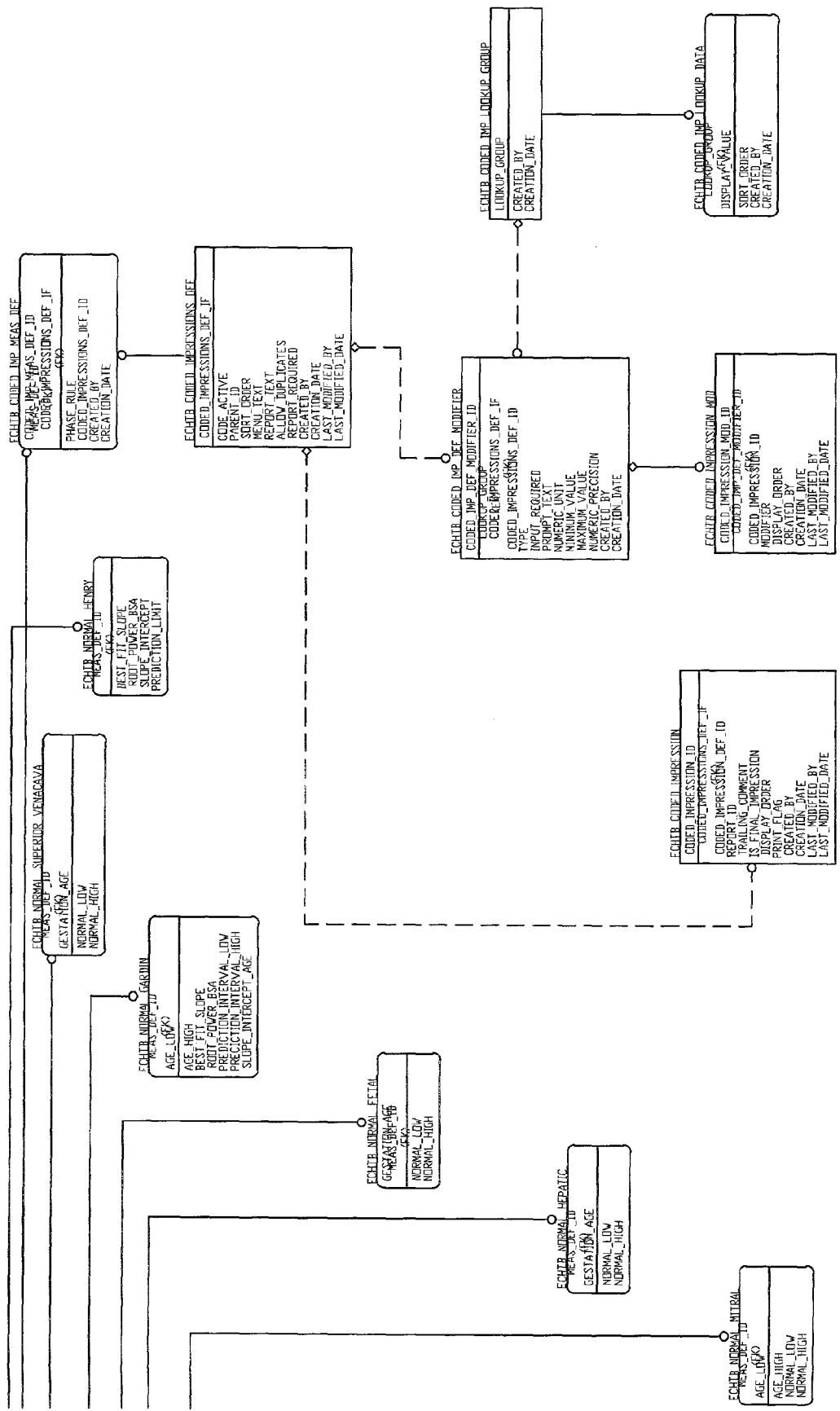
Figure 5F:
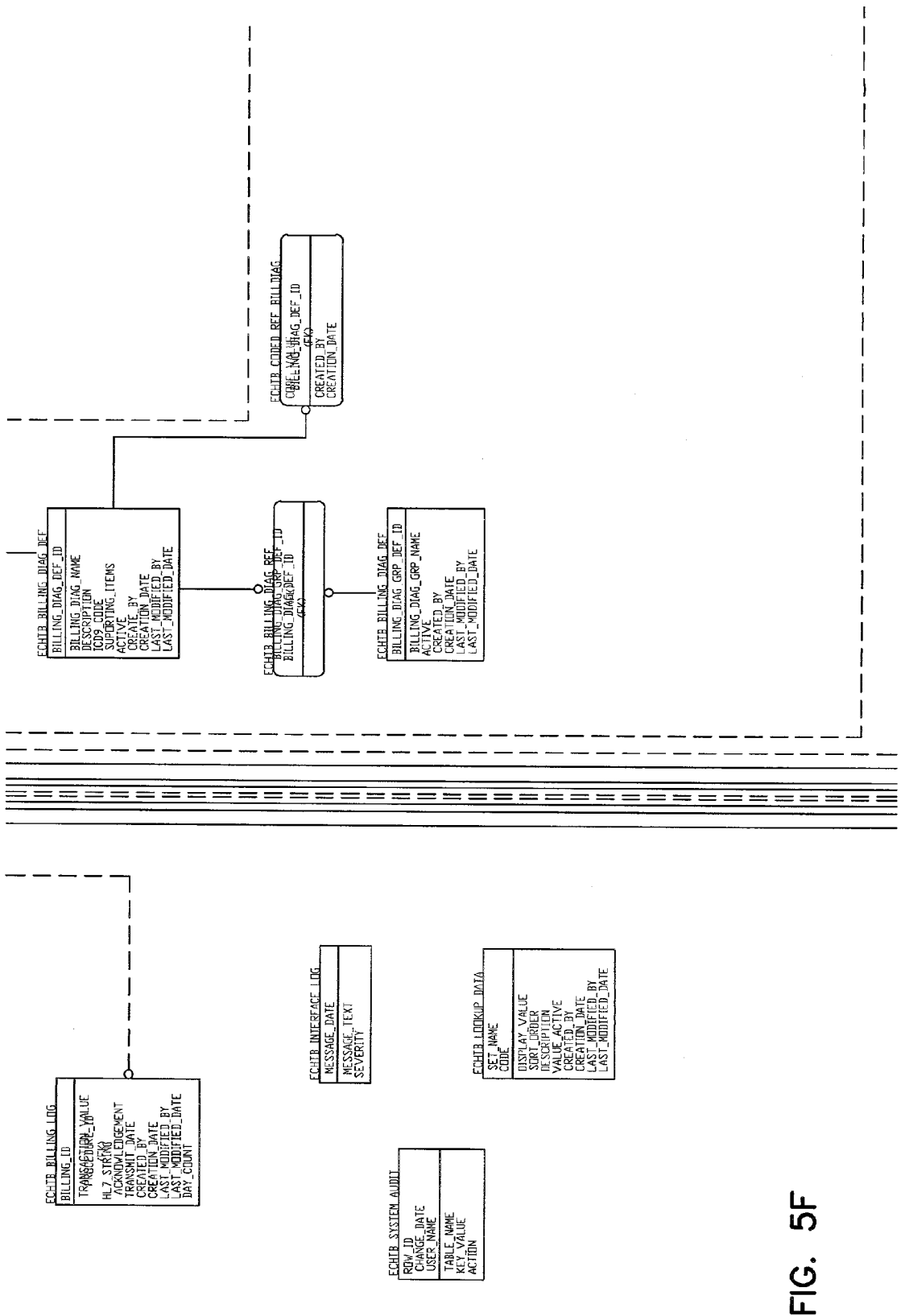
Figure 5G:
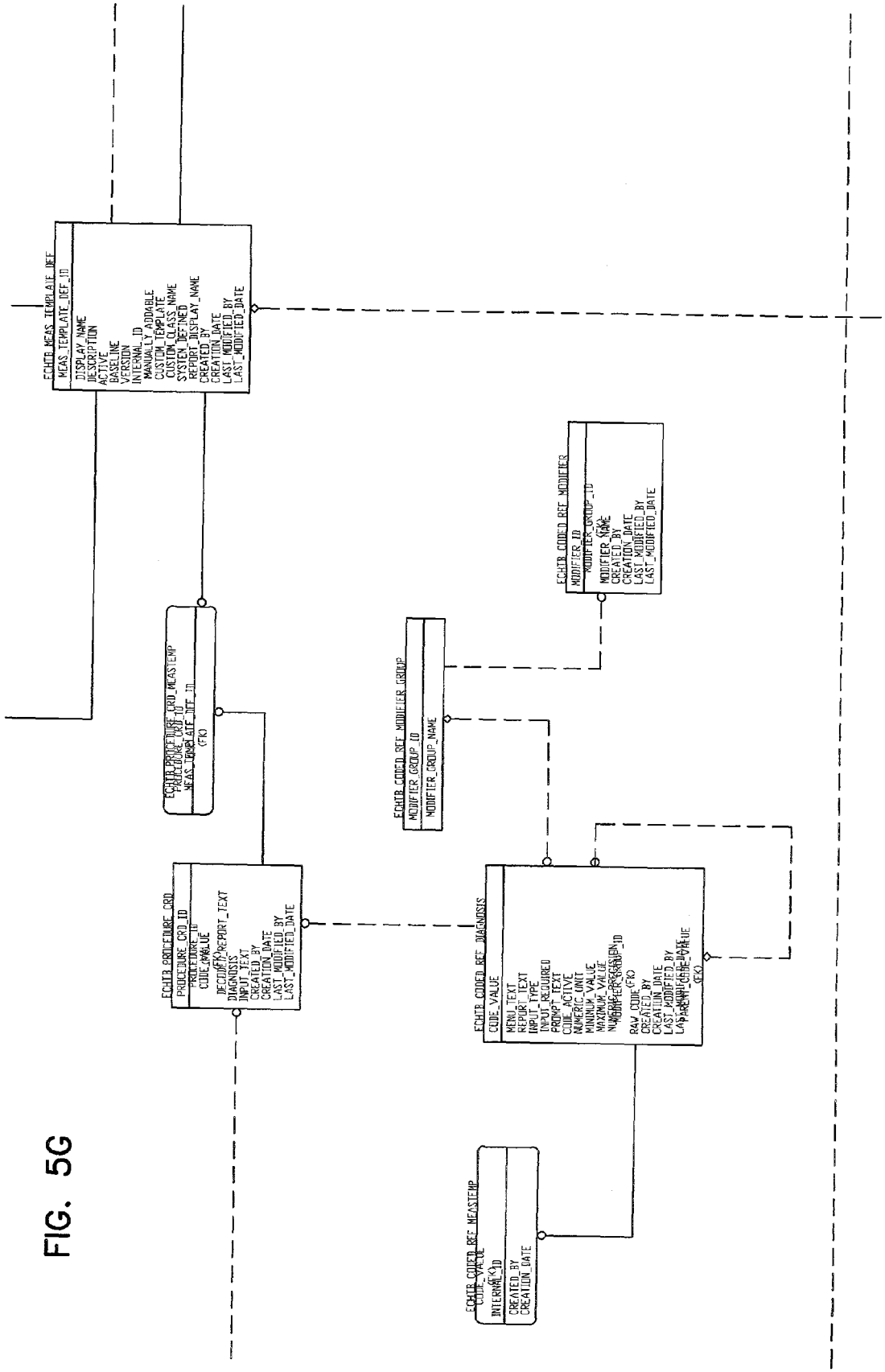
Figure 5H:
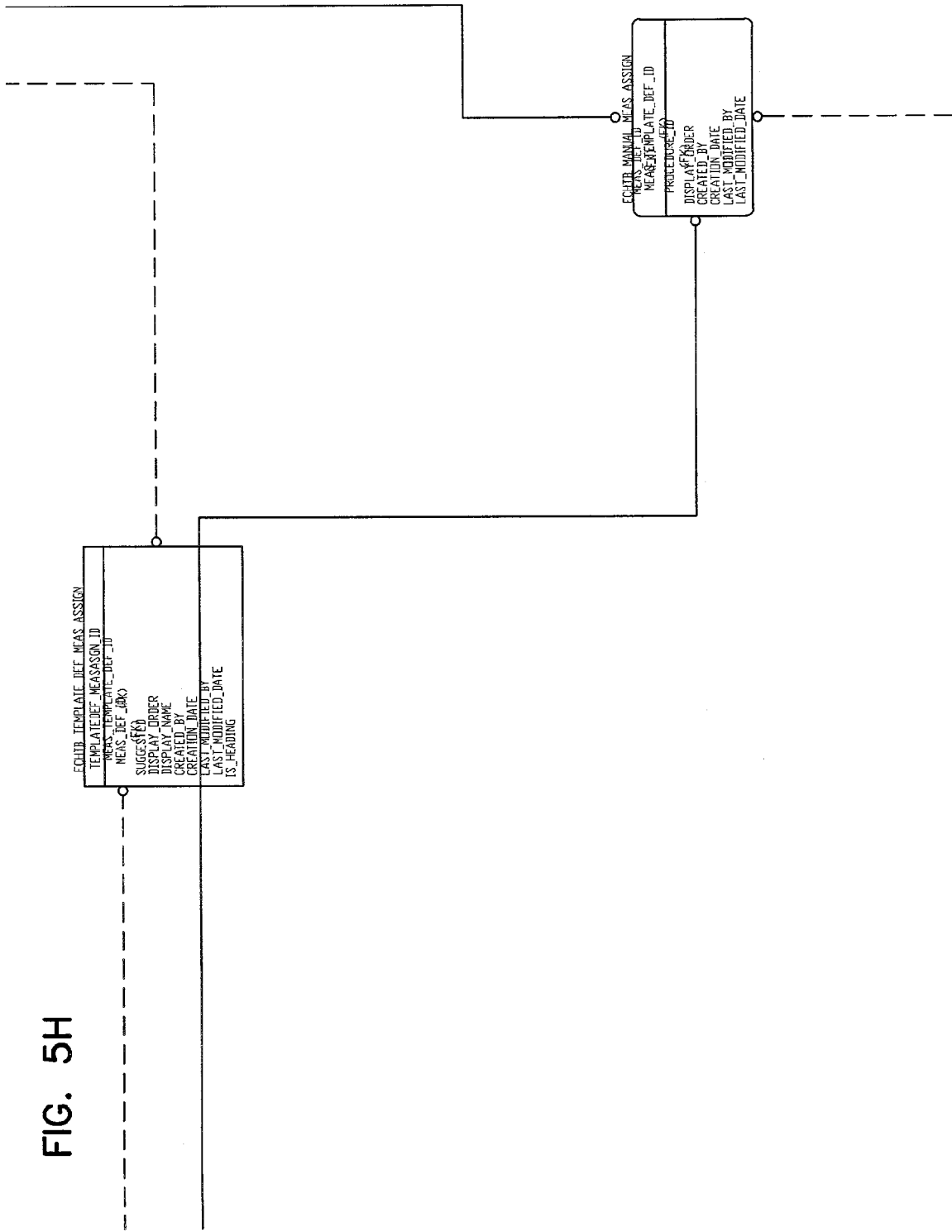
Figure 51:
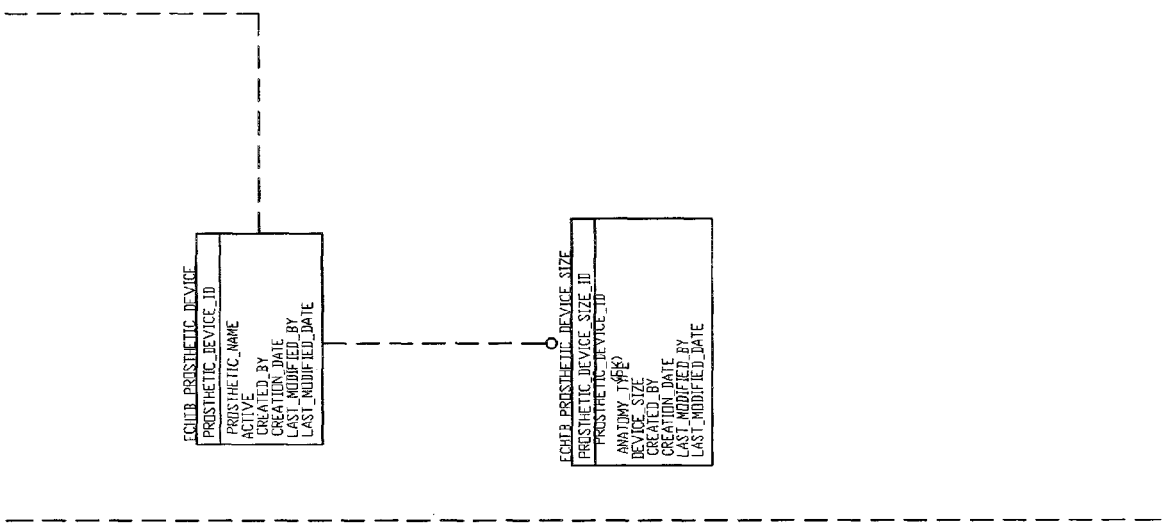
Figure 5K:
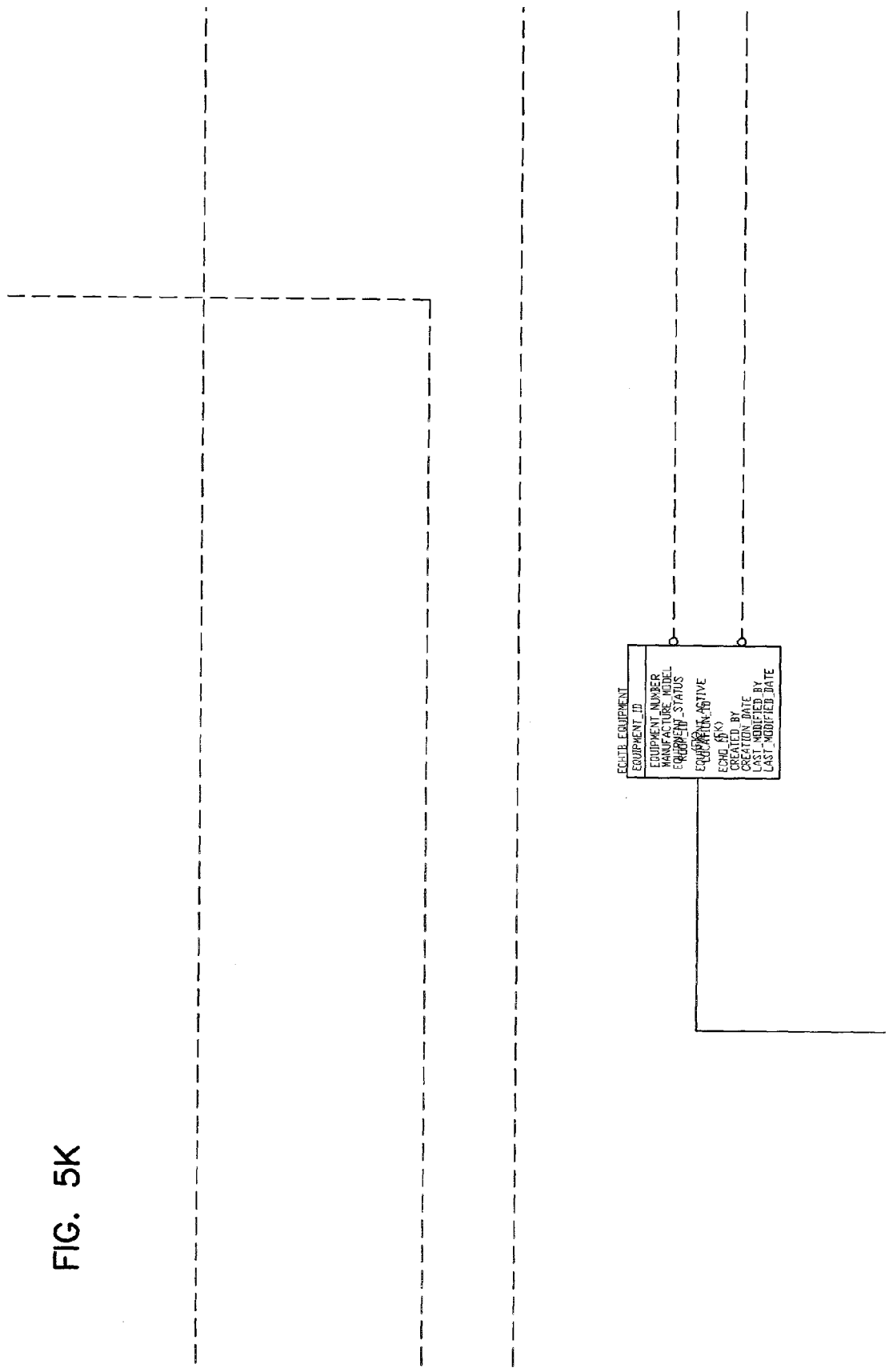
Figure 5L:
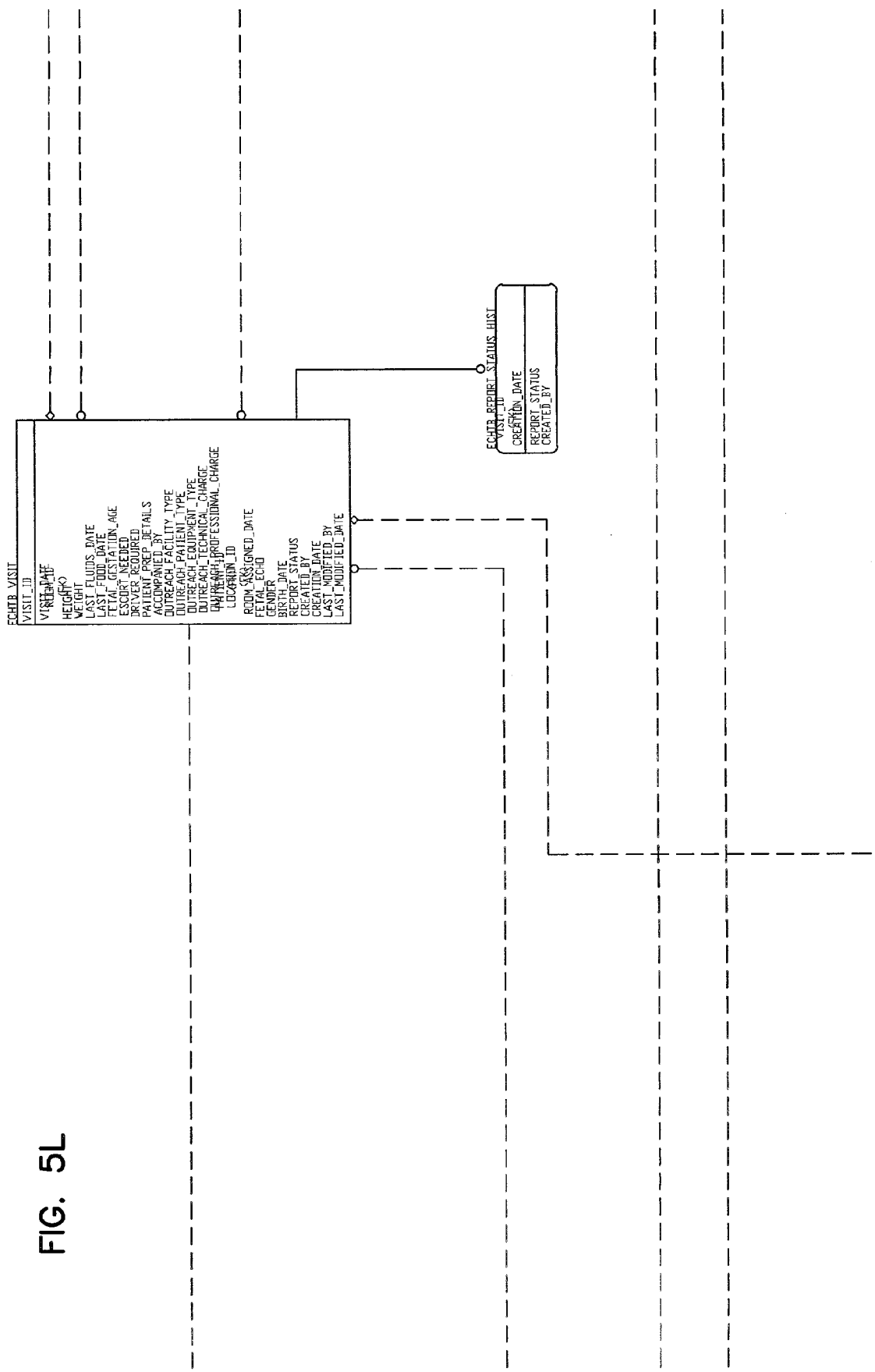
Figure 5M:
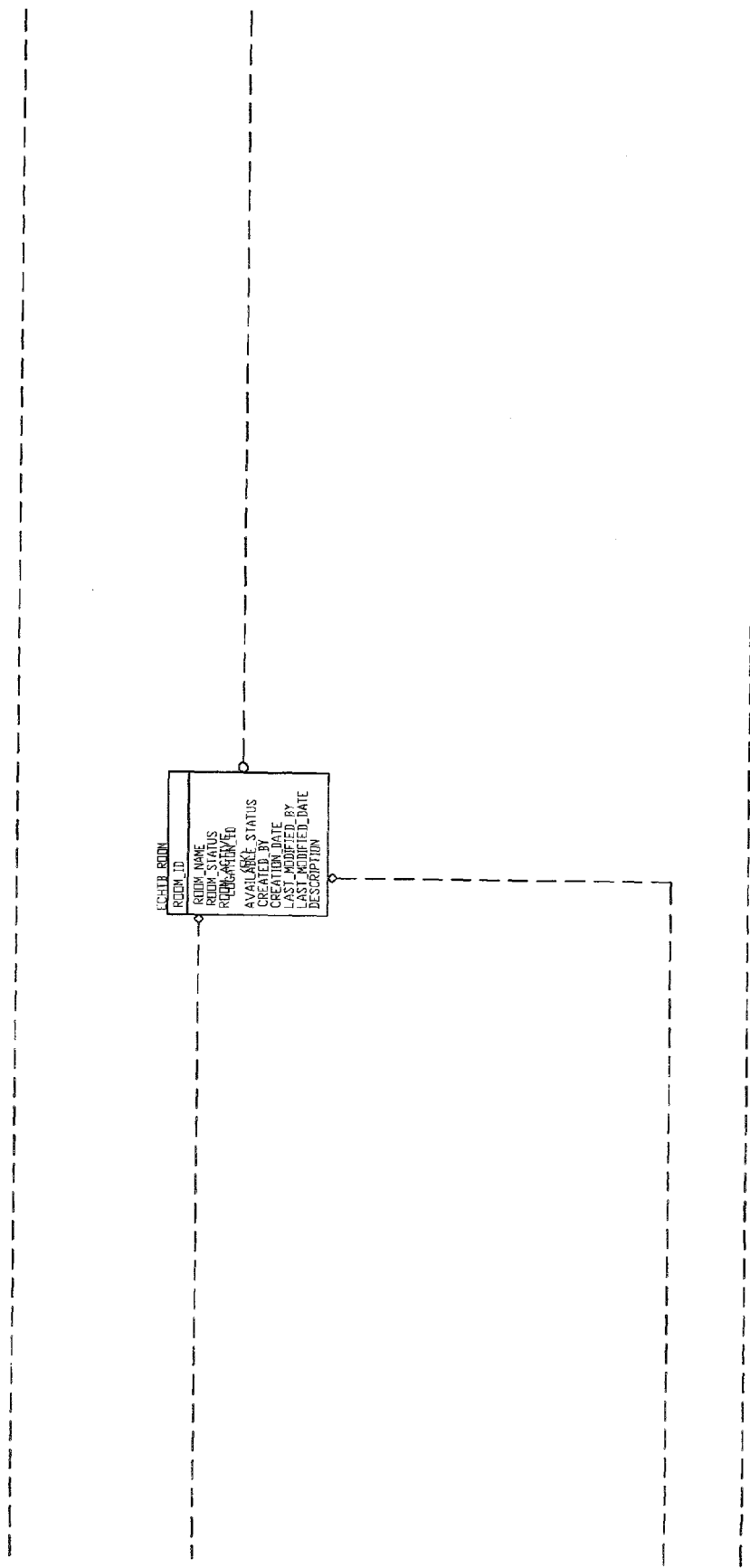
Figure 5N:
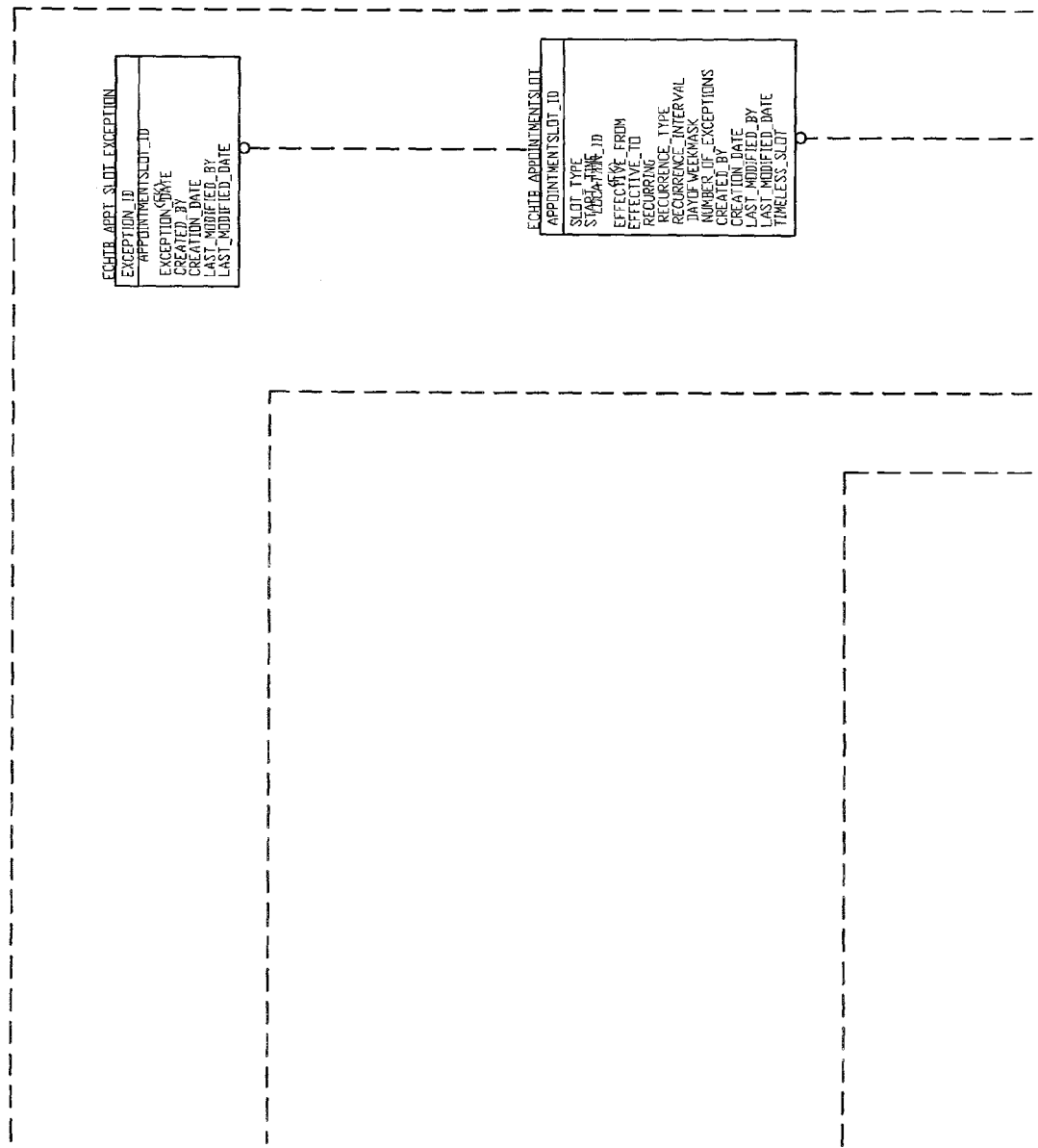
Figure 50:
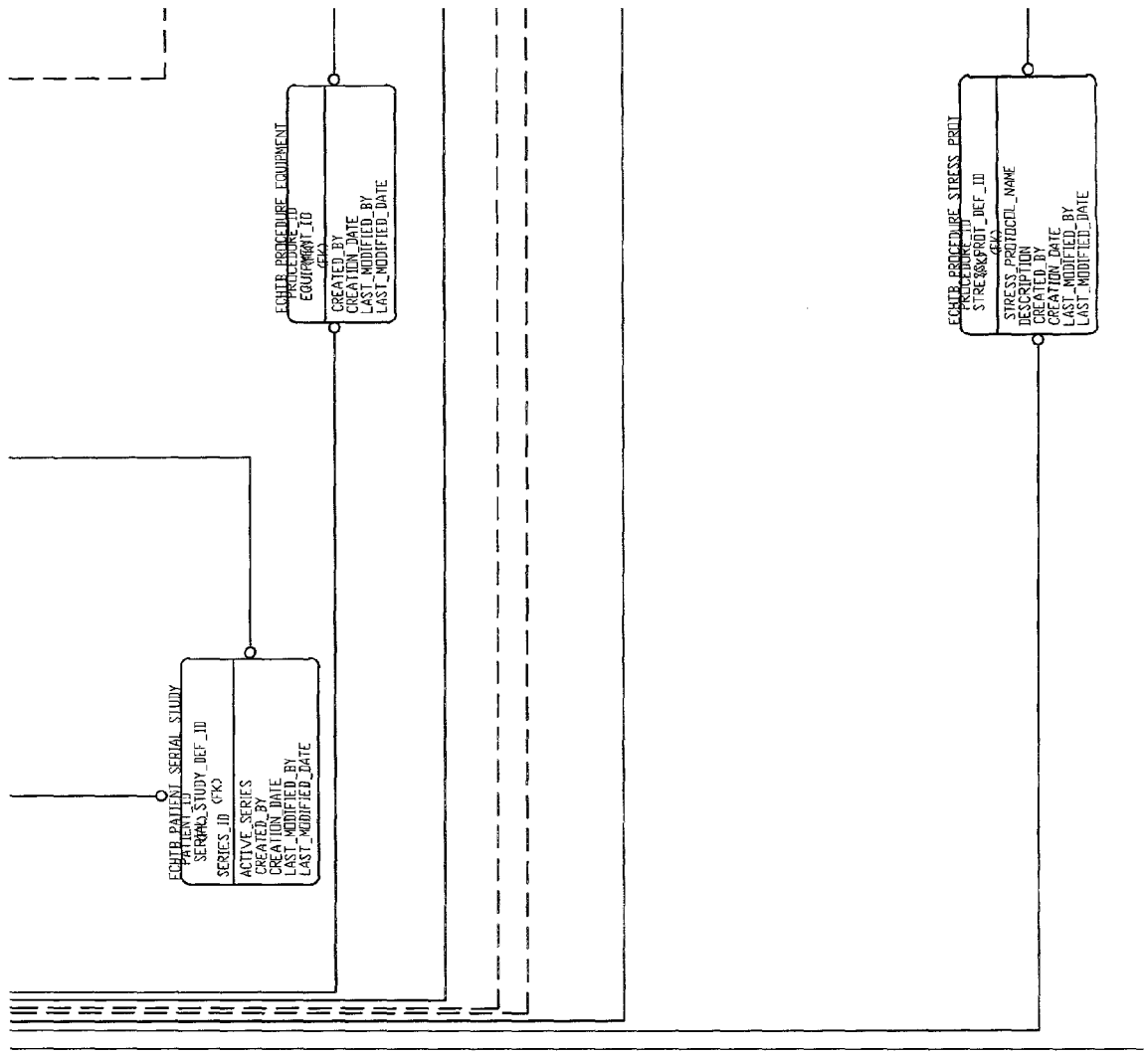
Figure 5Q:
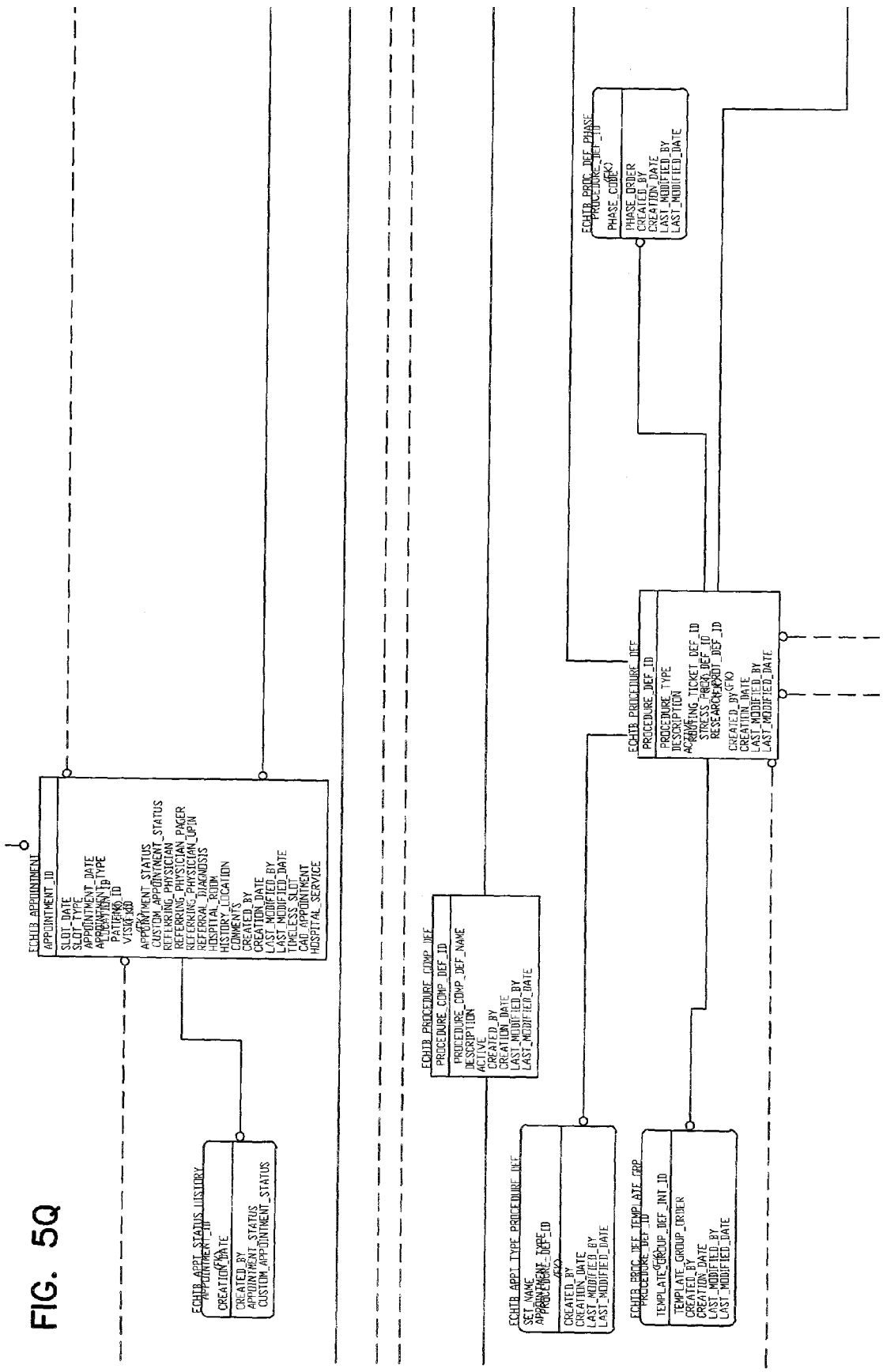
Figure 5R:
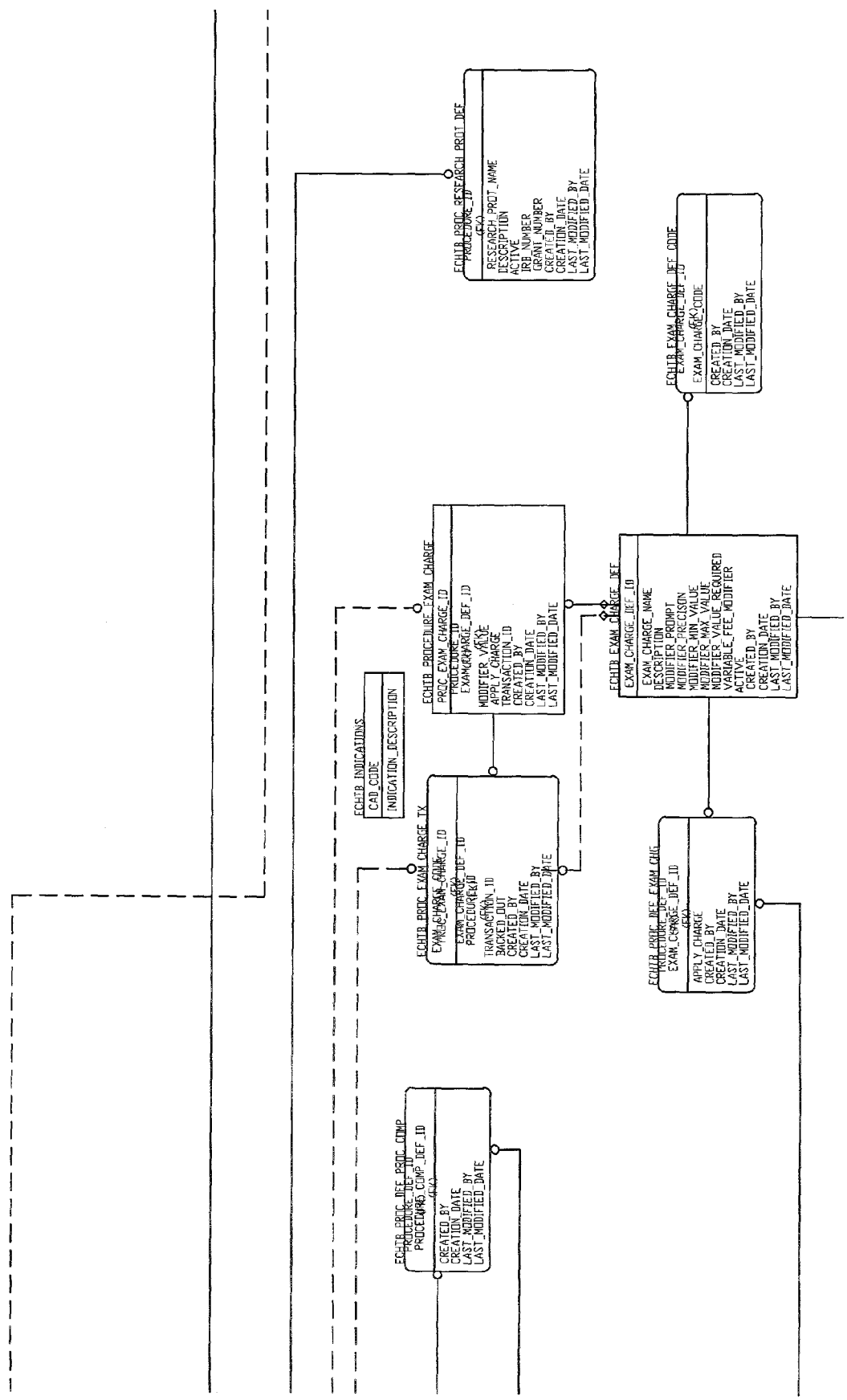
Figure 5S:
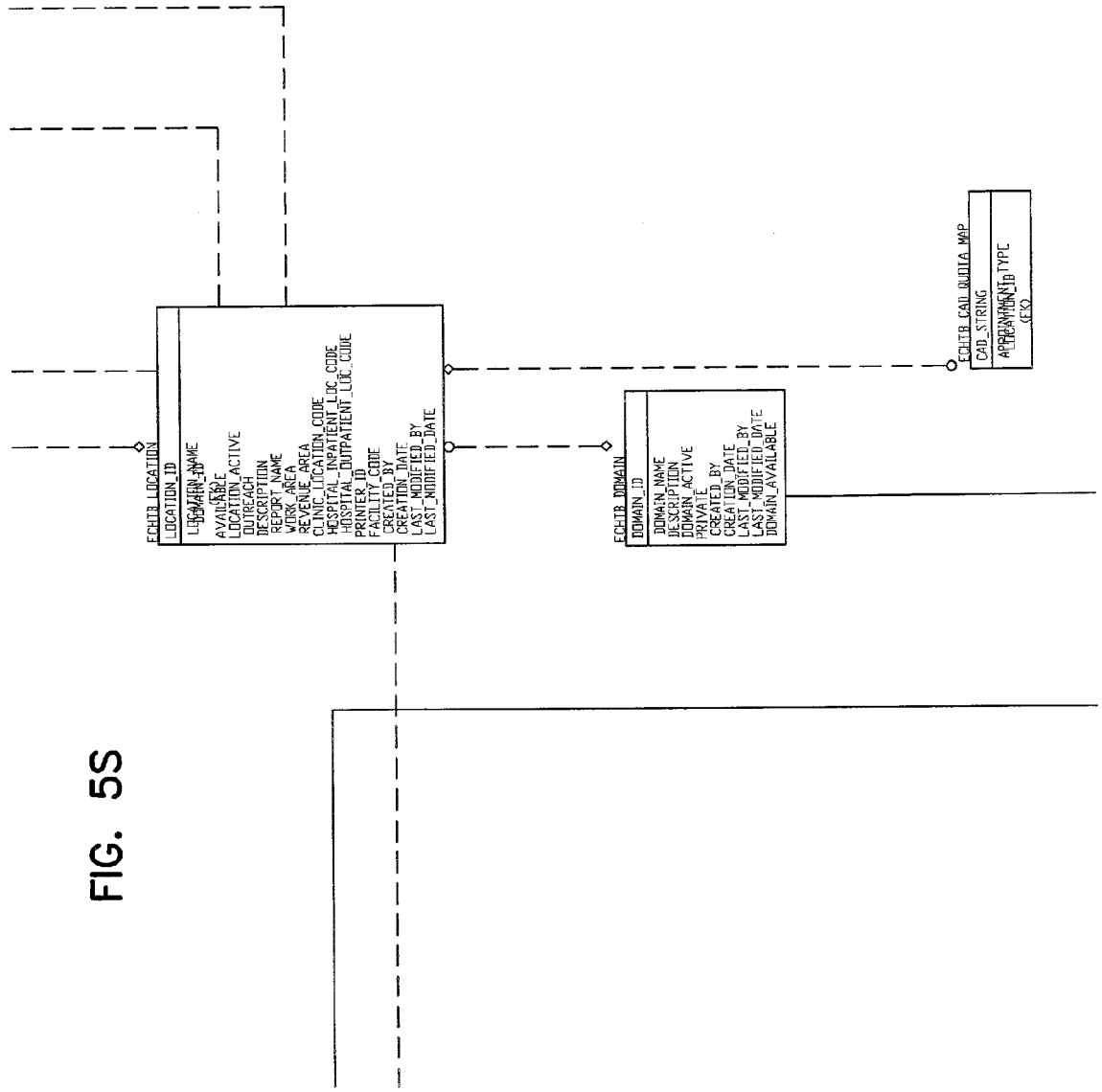
Figure 5T:
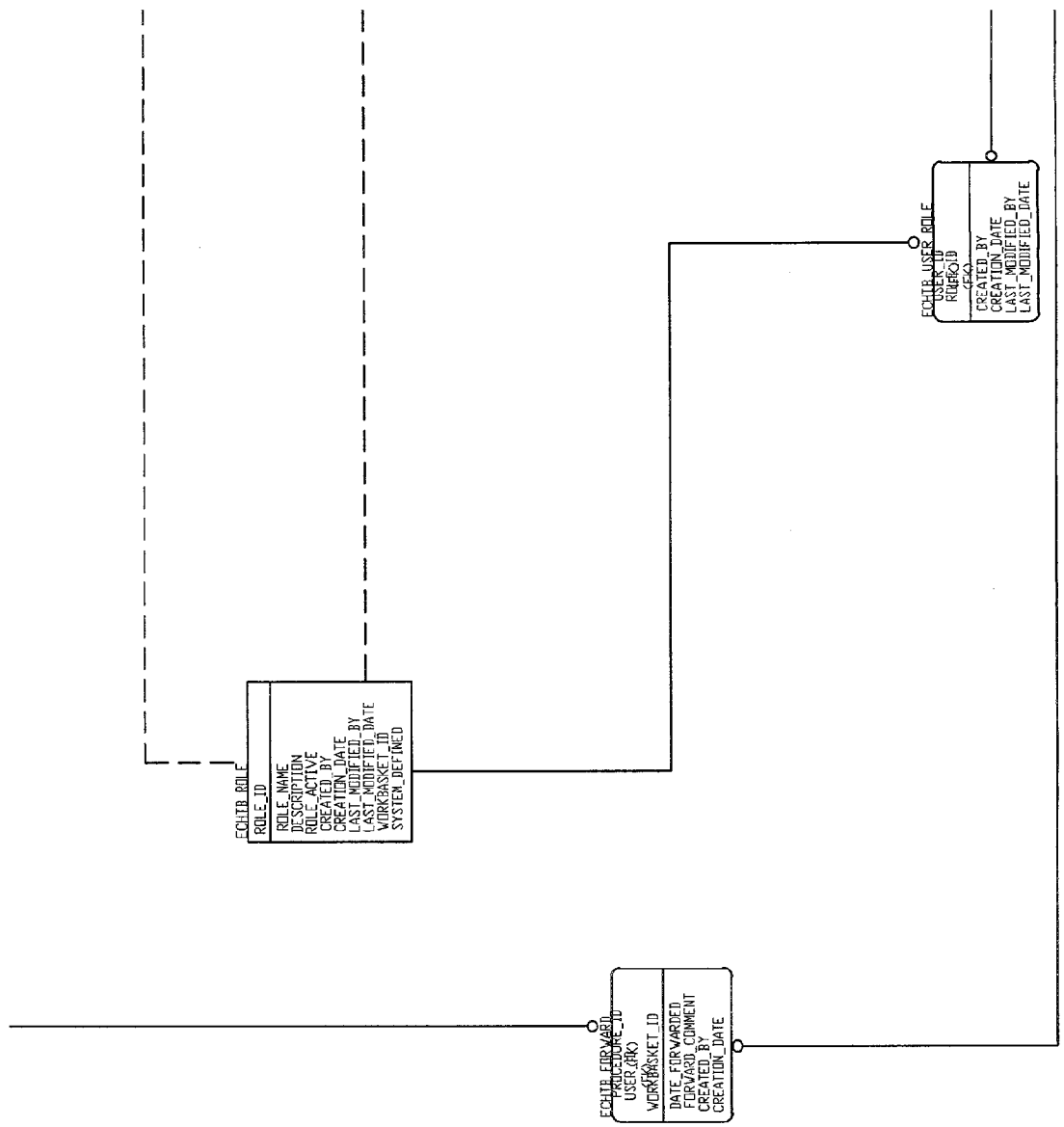
Figure 5U:
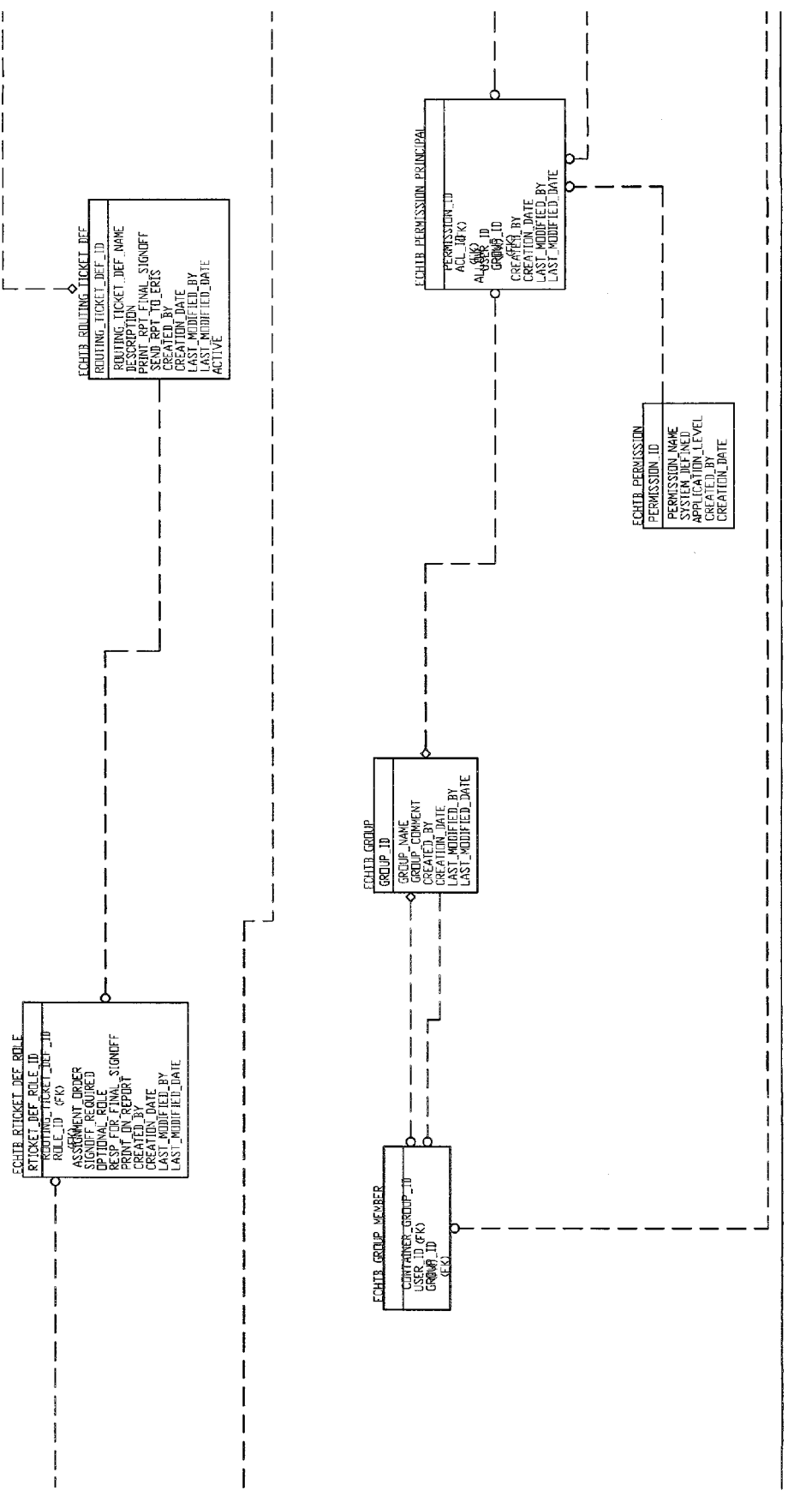
Figure 5V:
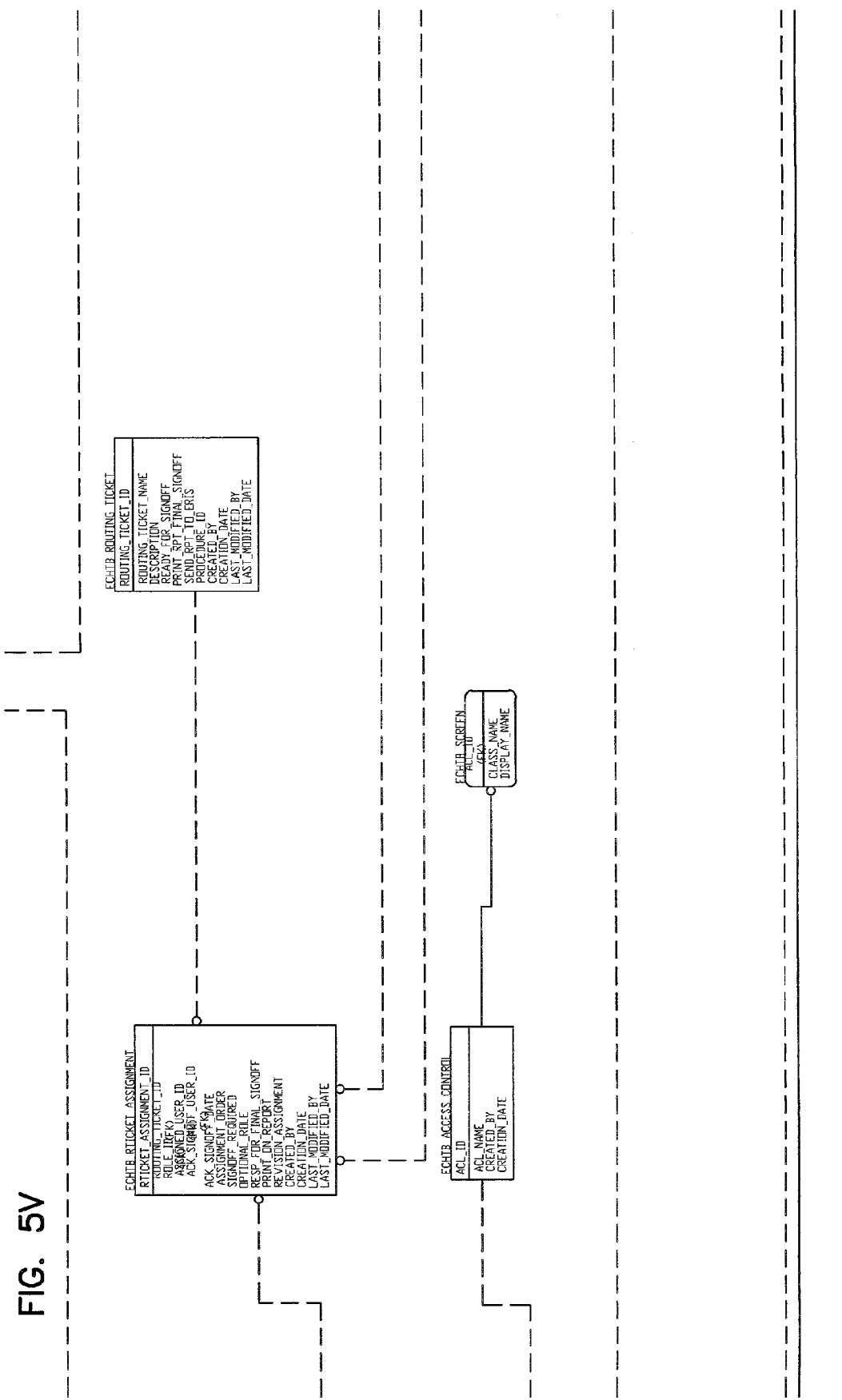
Figure 5W:
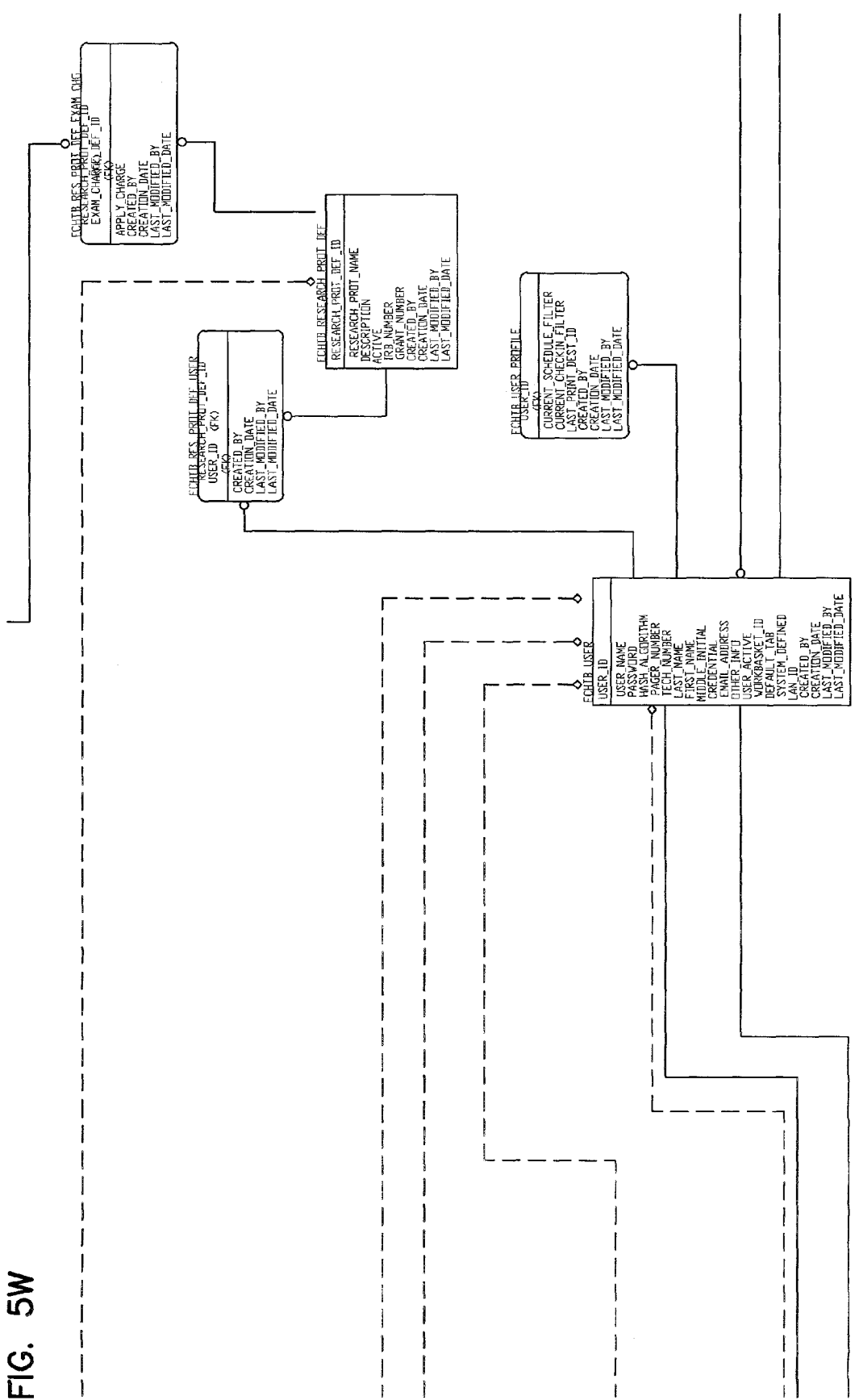
Figure 5X:
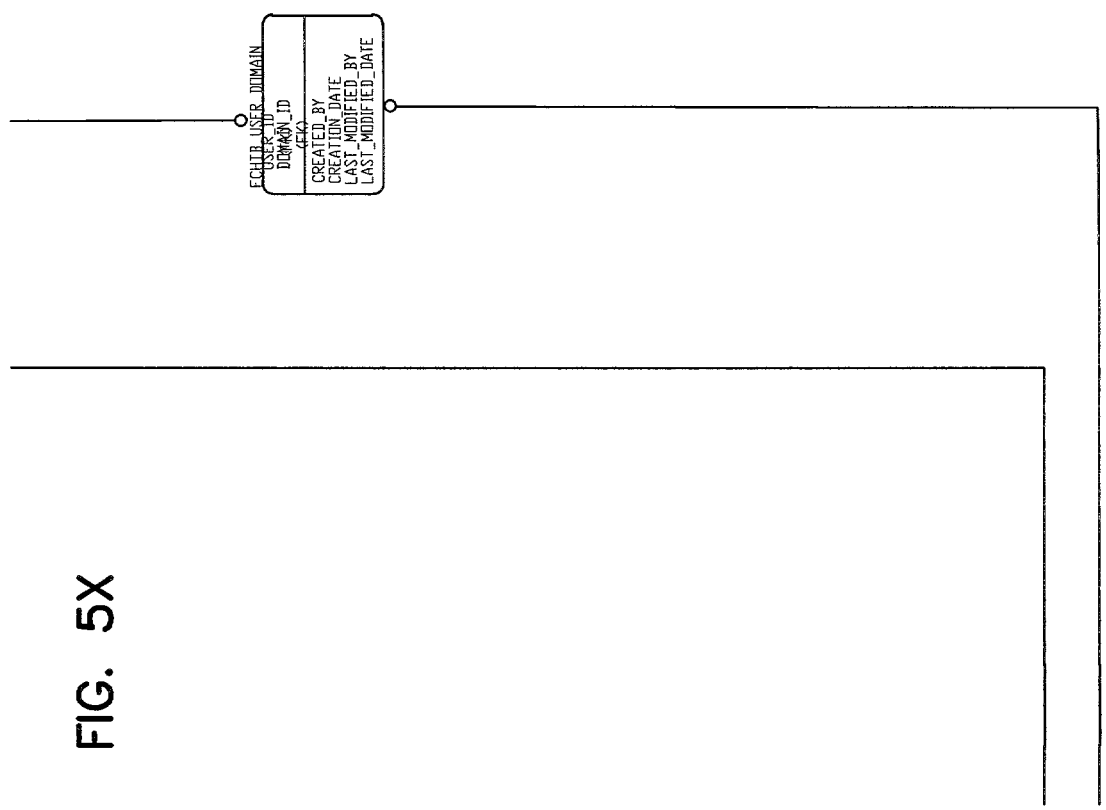

Referring now to FIG. 5A, an exemplary table 202 within table layout 200 includes a table title 204, a table header 208, and table data 206. Table header 208 and table data 206 may include one or a plurality of data elements 210, and some data elements 210 may be designated primary or secondary indexing keys. In the interest of clarity, each table 202 within table layout 200 has not been labeled but is understood to include the same structure described above.

Between tables within table layout 200 are a plurality of table linkages 212, indicated by both dashed and solid lines, which may include end symbols 214 including diamonds and circles, some of which are labeled on FIG. 5A. In the interest of clarity, each table linkage 212 and end symbol 214 within table layout 200 has not been labeled but is understood to indicate a logical link defined between data elements 210 inside the tables. The various lines 212 and end symbols 214 indicate the nature of the relationship between data tables 202 connected by lines 212.

The foregoing description of the exemplary embodiment of the invention has been presented for the purposes of illustration and description. It is not intended to be exhaustive or to limit the invention to the precise form disclosed. Many modifications and variations are possible in light of the above teaching. It is intended that the scope of the invention be limited not with this detailed description, but rather by the claims appended hereto.

What is claimed is as follows:

1. An ultrasound laboratory information system comprising:
   a. a plurality of ultrasound DICOM devices that gather ultrasound image and measurement data information;
   b. a plurality of computer software modules that obtain measurements and an initial impression, store the ultrasound image and ultrasound measurement data received from the ultrasound DICOM devices, and present the ultrasound image and textual data interpretation to users through a user interface, and allow free form user comments concerning the image;
   c. a communications network that communicates the ultrasound image and measurement data to the computer modules; and
   d. a knowledge base server connected to the communications network, the knowledge base server performing the following functions:
      i. maintaining a glossary of terms relating to the performance of an ultrasound laboratory;
      ii. analyzing the initial impression,
      iii. suggesting which measurements should be obtained with the ultrasound devices based on the analysis of the initial impression,
      iv. comparing the ultrasound measurement data received from the ultrasound DICOM devices against normal value ranges,
      v. determining valid ranges for the ultrasound measurement data based on the initial impression that support the initial impression and refute the initial impression,
      vi. indicating if data within the valid ranges has not been obtained and the ultrasound measurement data is thereby indicative of one of ultrasound DICOM device or clinician error,
      vii. analyzing whether the ultrasound measurement data supports the initial impression.

2. The ultrasound laboratory information system of claim 1, wherein the knowledge base server further performs the function of suggesting additional measurements to be obtained through additional ultrasound tests after analyzing whether the measurement data confirms the initial impression.

3. A method of managing information within an ultrasound imaging medical laboratory system comprising the steps of:
   a. maintaining within an artificial intelligence knowledge base a glossary of terms relating to the performance of an ultrasound imaging medical laboratory;
   b. permitting users to annotate impressions, measurements, and outcomes within the artificial intelligence base;
   c. inputting patient demographic information and an initial impression into the system;
   d. using an artificial intelligence knowledge base to analyze the initial impression and to suggest ultrasound measurements to be obtained through an ultrasound examination using ultrasound DICOM equipment;
   e. allowing the artificial intelligence feature of the knowledge base to analyze previous data for different subjects in order to adapt the suggested ultrasound measurements to a particular subject;
   f. analyzing, by the artificial intelligence feature of the knowledge base, previous data for different subjects in order to adapt the suggested ultrasound measurements to a particular subject;
   g. receiving ultrasound image and ultrasound measurement data from the ultrasound DICOM equipment; and
   h. using the knowledge base to analyze the ultrasound measurement data by:
      i. comparing the ultrasound measurement data against normal value ranges,
      ii. determining valid ranges for the ultrasound measurement data based on the initial impression that support the initial impression and refute the initial impression,
      iii. indicating if data within the valid ranges has not been obtained and the ultrasound measurement data is thereby indicative of one of ultrasound DICOM device or clinician error,
      iv. analyzing whether the ultrasound measurement data supports the initial impression, and v. suggesting additional ultrasound measurements to be obtained after analyzing whether the ultrasound measurement data confirms the initial impression.

4. The ultrasound laboratory information system of claim 1, wherein the function of analyzing the ultrasound measurement data includes comparing the ultrasound measurement data against expected data based in part upon patient demographic information and other physical characteristics of a patient.

5. The ultrasound laboratory information system of claim 1, wherein the functions performed by the knowledge base server further comprises:
    viii. after measurement data from the ultrasound devices has been validated against information in the knowledge base, informing a user if the objectives of the procedure have been met.

\* \* \* \* \*

UNITED STATES PATENT AND TRADEMARK OFFICE
CERTIFICATE OF CORRECTION

PATENT NO. : 8,417,536 B2
APPLICATION NO. : 10/150646
DATED : April 9, 2013
INVENTOR(S) : James B. Seward et al.

It is certified that error appears in the above-identified patent and that said Letters Patent is hereby corrected as shown below:

Title Page, Item (75) 3rd Inventor "James" should be -- Joel --

Signed and Sealed this
Twenty-first Day of May, 2013

Teresa Stanek Rea
*Acting Director of the United States Patent and Trademark Office*